United States Patent [19]
Hostetler

[11] Patent Number: 5,817,638
[45] Date of Patent: Oct. 6, 1998

[54] ANTIVIRAL LIPONUCLEOSIDES: TREATMENT OF HEPATITIS B

[75] Inventor: Karl Y. Hostetler, Del Mar, Calif.

[73] Assignee: NeXstar Pharmaceuticals, Inc., Boulder, Colo.

[21] Appl. No.: 456,537

[22] Filed: Jun. 1, 1995

Related U.S. Application Data

[62] Division of Ser. No. 222,571, Apr. 4, 1994, which is a continuation of Ser. No. 730,273, Jul. 12, 1991, abandoned, which is a continuation-in-part of Ser. No. 373,088, Jun. 28, 1989, Pat. No. 5,223,263, which is a continuation of Ser. No. 319,485, Mar. 6, 1989, abandoned, which is a continuation of Ser. No. 216,412, Jul. 7, 1988, abandoned.

[51] Int. Cl.$^6$ ................................................ A61K 31/70
[52] U.S. Cl. ............................... 514/45; 514/46; 514/47; 514/48; 514/49; 514/50; 514/51; 514/894; 424/450; 536/26.23; 536/26.26; 536/26.7; 536/26.8; 536/26.9; 536/27.14; 536/28.2
[58] Field of Search .............................. 424/450; 514/45, 514/49, 50, 51, 894; 536/26.23, 26.26, 26.27, 26.8, 26.9, 27.14, 28.2

[56] References Cited

U.S. PATENT DOCUMENTS

| | | |
|---|---|---|
| 4,283,394 | 8/1981 | West . |
| 4,291,024 | 9/1981 | Turcotte . |
| 4,429,008 | 1/1984 | Martin et al. . |
| 4,464,359 | 8/1984 | Suhadolnik et al. . |
| 4,471,113 | 9/1984 | MacCoss . |
| 4,533,254 | 8/1985 | Cook et al. . |
| 4,579,849 | 4/1986 | MacCoss . |
| 4,605,645 | 8/1986 | Watanabe et al. . |
| 4,622,392 | 11/1986 | Hong et al. . |
| 4,670,424 | 6/1987 | MacCoss . |
| 4,692,433 | 9/1987 | Hostetler et al. . |
| 4,737,323 | 4/1988 | Martin et al. . |
| 4,797,479 | 1/1989 | Shuto . |
| 4,810,697 | 3/1989 | Spieser et al. . |
| 4,921,951 | 5/1990 | Shuto et al. . |
| 4,997,926 | 3/1991 | Haertle et al. . |
| 5,026,558 | 6/1991 | Hwang . |
| 5,039,667 | 8/1991 | Tyrrell et al. . |
| 5,149,794 | 9/1992 | Yatvin t al. . |
| 5,194,654 | 3/1993 | Hostetler et al. . |
| 5,512,671 | 4/1996 | Piantadosi et al. ................. 536/26.1 |

FOREIGN PATENT DOCUMENTS

| | | |
|---|---|---|
| 056 265 | 7/1982 | European Pat. Off. . |
| 122 151 | 10/1984 | European Pat. Off. . |
| 199 451 | 10/1986 | European Pat. Off. . |
| 254 268 | 1/1988 | European Pat. Off. . |
| 262 876 | 4/1988 | European Pat. Off. . |
| 8830730 | 8/1988 | European Pat. Off. . |
| 286 418 | 12/1988 | European Pat. Off. . |
| 306 597 | 3/1989 | European Pat. Off. . |
| 311 100 | 4/1989 | European Pat. Off. . |
| 2168350 | 6/1986 | United Kingdom . |
| WO 94/03465 | 2/1974 | WIPO . |
| 8901776 | 2/1985 | WIPO . |
| WO 88/07532 | 10/1988 | WIPO . |
| WO 89/02733 | 6/1989 | WIPO . |
| WO 90/00555 | 1/1990 | WIPO . |
| WO 91/09602 | 7/1991 | WIPO . |
| WO 91/18914 | 12/1991 | WIPO . |
| WO 91/19726 | 12/1991 | WIPO . |
| WO 92/03462 | 3/1992 | WIPO . |
| WO 93/16091 | 8/1993 | WIPO . |
| WO 93/16092 | 8/1993 | WIPO . |
| WO 94/25046 | 11/1994 | WIPO . |

OTHER PUBLICATIONS

Acs, G. et al. Hepatitis B virus produced by transfected Hep G2 cells causes hepatitis in chimpanzees, *Proc. Nat. Acad. Sci.* 84:8581 (1987).

Agranoff, B. and Suomi, W. Cytidine diphosphate–DL–dipalmitin *Biochem. Prep.* 10:46–51 (1963).

Bligh E. and Dyer. W. A rapid method of total lipid extraction and purification. *Can. J. of Biochem. and Phys.* 37:911–917 (1957).

Brown, D., et al. An X–ray examination of long–chain alkyl dihydrogen phosphates. *J. Chem. Soc.* (London) 1584–1855 (1955).

Fukanaga, M., et al. Liposome entrapment enhances the hypocalcemic action . . . *Endocrinol.* 16:757–761 (1984).

Hantz, O. et al. Inhibition of human and woodchuck hepatitis virus DNA polymerase . . . *Antiviral Research* 4:187–199 (1984).

Hess, G. et al. Inhibition of hepatitis B virus deoxyribonucleic acid polymerase . . . *Antimicrobial Agents and Chemotherapy* 19(1):44–50 (1981).

Kassanides, C. et al. Inhibition of duck hepatitis B virus replication . . . *Gastroenterology* 97:1275–80 (1989).

Kim, S., et al. Preparation of multivesicular liposomes. *Biochim. Biophys. Acta* 728:339–348 (1982).

Lee, B. et al. In vitro and in vivo comparison of the abilities of purine . . . *Antimicrobial Agents and Chemotherapy* 33:336–339 (1989).

Matthes, E. et al. Potent inhibition of hepatitis B virus production in vitro . . . *Antimicrobial Agents and Chemotherapy* 34:1986–1990 (1990).

Mayhew, E., et al. Characteristics of liposomes prepared using a microemulsifier. *Biochim. Biophys. Acta* 775:169–175 (1984).

(List continued on next page.)

*Primary Examiner*—James O. Wilson
*Attorney, Agent, or Firm*—Swanson & Bratschun, L.L.C.

[57] ABSTRACT

Compounds for treating hepatitis B infections. The compounds consist of nucleoside analogues having anti-hepatitis B activity which are linked, commonly through a 5' phosphate of the pentose residue, to one of a selected group of lipids. The lipophilic nature of these compounds provides an advantage over the use of the nucleoside analogue alone, making it possible to incorporate them into the lamellar structure of liposomes, either alone or in combination with similar lipid molecules. In the form of appropriately sized liposomes, these anti-hepatitis B agents are preferentially taken up by the liver cells which have been found to harbor the target virus.

13 Claims, 3 Drawing Sheets

OTHER PUBLICATIONS

Mayer, L.D., et al. Vesicles of variable sizes produced by a rapid extrusion procedure. *Biochim. Bophys. Acta* 858:161–168 (1986).

Olson, F., et al. Preparation of liposomes of defined size distribution . . . *Biochim. Biophys. Acta* 557:9–23 (1979).

Rosenthal, A. and Geyer, R. A Synthetic inhibitor of venom lecithinase A. *Journal of Biol. Chem.* 235(8):2202–2206 (1960).

Sherphof, G. L. et al. In vivo uptake and processing of liposomes . . . NATO ASI *Series, Ser. A: Targeting Drugs* 155:109–120 (1988).

Sherphof. G.L. et al. Liposomes in chemo–and immunotherapy of cancer. *Lipids* 22(11)891–896 (1987).

Spanjer, H. et al. Intrahepatic distribution of small unilamellar liposomes . . . *Biochim. Biophys. Acta* 863:24–230 (1986).

Szoka, F., and Papahadjopoulos, D. Procedure for preparation of liposomes . . . *Proc. Nat. Acad. Sci.* 75:4194–4198 (1978).

Toorchen, D. and Topal, M. Mechanisms of chemical mutagenesis and carcinogenesis: effects on DNA . . . *Carcinogenesis* 4:1591–1597 (1983).

Yoshikawa, M., et al. Studies of phosphorylation. III. Selective phosphorylation . . . *Bull. Chem. Soc. Japan* 42:3205–3208 (1967).

Yoshikawa, et al. A novel method for phosphorylation of nucleosides to 5'–nucleotides. *Tetrahedron Lett.* 4 50:5065–5068 (1967).

Richman, et al. (1987), "Failure of dideoxynucleosides to inhibit human immunodeficiency virus replication in cultured human macrophages," J. Exp. Med., 166:1144–1149.

Fischl, et al. (1987), "The efficacy of Azidothymidine (AZT) in the treatment of patients with AIDS and AIDS–related complex," New Eng. J. Med., 317:185–191.

Richman, et al. (1987), "The toxicity of azidothymidine (AZT) in the treatment of patients with AIDS and AIDS–related complex," New Eng. J. Med., 317:192–197.

Bangham, et al. (1965), "Diffusion of univalent ion across the lamellae of swollen phospholipids," J. Mol. Biol., 23:238–252.

Black, et al. (2977), "The use of pentostam liposomes in the chemotherapy of experimental leishmaniasis," Trans. Roy. Soc. Trop. Med. Hyg., 71:550–52.

Alving, et al. (1978), "Therapy of leishmaniasis: Superior efficacies of liposome–encapsulated drugs," PNAS USA, 75:2959–63.

Lopez–Berestein, (1986), "Liposomal Amphotericin B in the treatment of fungal infections," Ann. Int. Med., 103:694–699.

Herman, et al. (1983), "Prevention of chronic doxorubicin cardiotoxicity in beagles by liposomal encapsulation," Cancer Res., 43:5427–32.

Ostro (1987), "Liposomes," Sci. Am., 256:103–111.

Salahuddin, et al. (1985), "Human T cell lymphotropic virus type III infection of human alveolar macrophages," Blood, 68:281–84.

Koenig, et al. (1986), "Detecting of AIDS virus in macrophages in brain tissue from AIDS patients with encepalopathy," Science, 233:1089–93.

Poste, et al. (1984), "The challenge of liposome targeting in vivo," in Liposome Technology, vol. III, G. Gregoriadis, ed., CRC Press, Boca Raton, pp. 1–28.

Scherphof (1986), "Liposomes in biology and medicine (a biased review)," in Lipids and Biomembranes, Past Present and Future, op den Kamp, J., Roelofsen, B. and Sirtz, K.W.A., eds., Elsevier, North Holland, Amsterdam, pp. 113–136.

Norley, et al. (1987), "Targeting of drug loaded immunoliposomes to herpes simplex virus infected corneal cells: an effective means of inhibiting virus replication in vitro," J. Immunol. 136:681–85.

Kende, et al. (1985), "Enhanced efficacy of liposome–encapsulated rebavirin against rift valley fever virus infection in mice," Antimicrob. Agents Chemother., 27:903–907.

Matsushita, et al. (1981), "Phospholipid derivative of nucleoside analogs as prodrugs with enhanced catabolic stability," Cancer Res., 41:2707–13.

Ho, et al. (1977), "Pharmacology of 5'–esters of 1–β–D–arabinofuranosylcytosine," Cancer Res., 37:1640–43.

Huang, et al. (1980), "Monoclonal antibody covalently coupled with fatty acid," J. Biol. Chem., 255:8015–18.

Leserman et al. (1980), "Targeting to cells of fluorescent liposomes covalently coupled with monoclonal antibody or protein A," Nature, 288:602–4.

Prottey, et al. (1967), "The biosynthesis of phosphatidic acid and phosphatidylinositol in mammalian pancreas," Biochem. J., 105:379–92.

Poorthuis, et al. (1976), "Studies on nucleotide diphosphate diacylglycerol specificity of acidic phospholipid biosynthesis in rat liver subcellular fractions," Biochim, Biophys. Acta, 431:408–15.

ter Scheggett, et al. (1971), "The synthesis and utilization of dCDP–diglyceride by a mitochondrial fraction from rat liver," Biochim. Biophys. Acta, 239:234–42.

Rittenhouse, et al. (1981), "Properties of a CDG–diglyceride hydrolase from guinea pig brain," J. Neurochem., 36:991–999.

Olson, et al. (1979), "Preparation of liposomes of defined size distribution by extrusion through a polycarbonate membrane," Biochim. Biophys. Acta, 557:9–23.

Heath (1986), "Liposome–mediated delivery of pteridine antifolates to cells in vitro: potency of methotrexate, and its α and γ substituents," Biochim. Biophys. Acta, 862:72–80.

Turcotte, et al. (1980), "I. Chemical synthesis of CDP–diacylglycerol analogs containing the cytosine arabinoside moiety," Biochim. Biophys. Acta, 619:604–608.

Turcotte, et al. (1980), "II. Antitumor activity of CDP–diacylglycerol analogs containing the cytosine arabinoside moiety," Biochim. Biophys. Acta, 619:619–31.

Murthy, et al. (1982), "Stereospecific synthesis and enzyme studies of CDP–diacylglycerols," Biochim. Biophys. Acta, 712:473–83.

Yang, et al. (1985), "Biophysical properties of cytidine diphosphate diacylglycerol in solution," Biochim. Biophys. Acta, 834:364–75.

Shuto, et al. (1986), "Synthesis of 5'–phosphatidylnucleosides by phospholipase D–catalyzed transphosphatidylation," Nucleic Acids Res.Symposium Series No. 17, pp. 73–76.

Carmen, et al. (1980), "Modification of the Agranoff–Suomi method for the synthesis of CDP–diacylglycerol," J. of Food Biochem., 42(1):53–59.

MacCoss et al. (1978), "The synthesis, characterization and preliminary biological evaluation of 1–β–D–arabinofuranosylcytosine–5'–diphosphate–L–1, 2–dipalmitin," Biochem. Biophys. Res. Commun., 85(2):714–23.

Raetz, et al. (1973), "Function of cytidine diphosphate diglyceride and deoxycytidine diphosphate–diglyceride in the biogenesis of membrane lipids in *E. coli*," J. Biol. Chem., 248(3):1098–1105.

Benjamins, et al. (1969), "Distribution and properties of CDP–diglyceride:inositol transferase from brain," J. Neurochem. 16:513–27.

Cao, et al. (1987), "Regulation by Vitamn E of phosphatidylcholine metabolism in rat heart," Biochem. J., 247:135–140.

Welch, et al. (1985), "The chemical synthesis and antiviral properties of an acyclovirphospholipid conugate," Acta Chem. Scand., B39, pp. 47–54.

Martin, et al. (1987), "Synthesis and antiviral activity of various esters of 9-[(1,3–dihydroxy–2–propoxy)methyl] guanine," J. Pharm. Sci., 76(2):180–84.

Lehninger (1975), Biochemistry, 2nd ed., Worth Publishers, Johns Hopkins Univeristy, pp. 291–294.

Ryu, et al. (1982), "Phospholipid–nucleoside conjugates, 3. Synthesis and preliminary biological evaluation of 1–β–D–arabinofuranosylcytosine–5'–monophosphate . . . " J. Med. Chem., 25:1322–29.

Berdel, et al. (1987), "Antineoplastic Activity of Conjugates of Lipids and 1–β–D–Arabinofuranosylcytosine", Lipids, 22(11):943–46.

Hostetler, et al. (1990), "Synthesis and Antiretroviral Activity of Phospholipid Analogs of Azidothymidine and Other Antiviral Nucleosides", J. Biol. Chem., 265:6112–17.

Nasr. et al. (1990), "Computer–assisted structure–activity correlations of dideoxynucleoside analogs as potential anti-–HIV drugs (mini–review)," Antiviral Res. 14:125–148.

Nasr, et al. (1992), "Computer–assisted structure–activity correlations of halodideoxynucleoside analogs as potential anti–HIV drugs," AIDS Res. and Human Retroviruses, 8:135–144.

Bennett, et al. (1975), "Studies on the Biochemical Basis For the Antiviral Activities of some Nucleoside Analogs," Ann. NY Acad. Sci., 255:342.

Montgomery (1986), "The Design of Chemotherapeutic Agents," ACC. Chem. Res., 19(10):293.

DeClercq, et al. (1980), "Antiviral, Antimetabolic and Antineoplastic Activites of 2'–or 3'–amino or –asido–substituted deoxyribonucleosides," Biochem. Pharmacol., 29:1849.

Mayhew et al., Biochimica et Biophysica Acta, vol. 775, pp. 169–174, (1984).

ANTIVIRAL LIPONUCLEOSIDES: TREATMENT OF HEPATITIS B

This application is a divisional of U.S. Ser. No. 08/222,571, filed Apr. 4, 1994; which is a continuation of U.S. Ser. No. 07/730,273, filed Jul. 12, 1991, now abandoned; which is a continuation-in-part of U.S. Ser. No. 07/373,088, filed Jun. 28, 1989, now U.S. Pat. No. 5,223,263; which is a continuation-in-part of U.S. Ser. No. 07/319,485, filed Mar. 6, 1989, now abandoned; which is a continuation-in-part of U.S. Ser. No. 07/216,412, filed Jul. 7, 1988, now abandoned.

BACKGROUND OF THE INVENTION

The present invention relates to the treatment of infections of hepatitis virus using lipid derivatives of antiviral nucleoside analogues. More particularly, the present invention relates to lipid, especially phospholipid, derivatives of antiviral nucleoside analogues which can be integrated into the structure of liposomes, thereby forming a more stable liposomal complex that can deliver greater amounts of antihepatitis drugs to target cells with less toxicity.

The publications and other reference materials referred to herein are hereby incorporated by reference, and are listed for convenience in the bibliography appended at the end of this specification.

Many nucleoside analogues are known to have activity against the hepatitis B virus (HBV). Recently, Lee et al. (1) as well as Kassanides et al. (2) have shown that dideoxynucleosides such as dideoxycytidine (ddC), dideoxyinosine (ddI), dideoxyadenosine (ddA), dideoxythymidine (ddT), dideoxyguanosine (ddG) and dideoxydiaminopurine are active against duck hepatitis B in vitro and in vivo (1,2). These drugs are thought to be effective because they inhibit a reverse transcriptase the hepatitis B virus utilizes at some stage of its life cycle. The triphosphates of other nucleosides such as acyclovir (ACV), bromovinyldeoxyuridine (BVdU), and deoxyfluoroarabinosyliodocytosine (FIAC) have also been reported to inhibit the DNA polymerase of hepatitis B virus from humans and woodchucks (3). The arabinofuranosyladenines (ara-A) and arabinofuranosyl-cytidines (ara-C) inhibit the human hepatitis B DNA polymerase, and ara-A has activity when administered to individuals suffering from chronic type B hepatitis (4). Further, Matthes et al. report that 2',3'-dideoxy-3'-fluorothymidine (FddThd), 2',3'-didehydro-2',3'-dideoxythymidine (ddeThd), 3'-fluoro-5-methyl-deoxycytidine (FddMeCyt), 3'-chloro-5-methyl-deoxycytidine ((ClddMeCyt), and 3'-amino-5-methyl-deoxycytidine (AddMeCyt) almost completely block production of hepatitis B virus particles in an HBV DNA-transfected cell line in vitro (5).

The antihepatitis B nucleoside analogues described above have very short half lives when administered to humans or animals as the free compound. After 4 to 6 hours, their levels in tissue and plasma are very low or negligible. These nucleoside analogues are also toxic, and their toxicity can be a limiting factor in therapeutic regimens. Clearly, it would be useful to administer the antihepatitis B nucleosides (dideoxynucleosides, acyclic nucleosides, and deoxynucleosides) in a form which could be targeted to the liver parenchymal cells, and which could maintain higher tissue levels over longer time periods.

SUMMARY OF THE INVENTION

The invention provides, in one embodiment, a compound having antiviral properties, comprising an antihepatitis B nucleoside analogue having a base portion comprising a purine or pyrimidine or analogue thereof, and a sugar portion comprising a pentose residue, wherein at least one the portion is a non-naturally occurring nucleoside component; and a lipid moiety linked to the pentose residue; with the proviso that the compound is in the form of a liposome when the pentose residue is arabinofuranose and the base portion is cytosine or adenine. The non-naturally occurring nucleoside component can be an analogue of a naturally occurring base or pentose by virtue of substitution, deletion, or replacement. In preferred embodiments, the pentose residue is a 2',3'-dideoxy, 2',3'-didehydro, or halo derivative of ribose, or an acyclic hydroxylated fragment of ribose. In particularly preferred embodiments, the pentose residue is a 2',3'-dideoxyribose, and the nucleoside analogue is 2',3'-dideoxycytidine; 2',3'-dideoxythymidine; 2',3'-dideoxyguanosine; 2',3'-dideoxyadenosine; 2',3'-dideoxyinosine; or 2,6-diaminopurine, 2',3'-dideoxyriboside. In other preferred embodiments, the pentose group is a halo- or an amino derivative of ribose and the nucleoside is 3'-fluoro-5-methyl-deoxycytidine (FddMeCyt),3'-chloro-5-methyl-deoxycytidine (ClddMeCyt), 3'-amino-5-methyl-deoxycytidine (AddMeCyt), or 2',3'-dideoxy-3'-fluorothymidine. The nucleoside analogue can alternatively be acyclovir, 1-(2'-deoxy-2'-fluoro-1-β-D-arabinofuranosyl)-5-iodocytosine (FIAC) or 1(2'-deoxy-2'-fluoro-1-β-D-arabinofuranosyl)-5-iodouracil (FIAU). In particularly preferred embodiments, the nucleoside analogue is 2',3'-didehydro-2',3'-dideoxythymidine.

The compounds described can further comprise a monophosphate, diphosphate, or triphosphate linking group between the 5' position of the pentose residue and the lipid moiety.

The lipid moiety of the compound can be a fatty acid, a monoacylglycerol or a diacylglycerol, a phosphatidic acid, a diphosphatidyl glycerol, a bis(diacylglycero)-phosphate, a D,L-2,3-diacyloxypropyl-(dimethyl)-β-hydroxyethyl ammonium group, or 1-O-stearoyl-rac-3-glycerol.

According to another embodiment, the invention provides a method for treating hepatitis B infection in a mammal, comprising administering to the mammal an effective hepatitis B virus-inhibiting dose of any of the compounds disclosed. The invention also provides a method for inhibiting the replication of hepatitis B virus in a cell, comprising contacting the cell with an effective hepatitis B virus-inhibiting dose of any of the compounds disclosed. In particular embodiments of this aspect of the invention, the hepatitis B virus infection is in a human cell, and the compound is phosphatidyl-dideoxycytidine (p-ddC), phosphatidyl-FIAC, FIAC diphosphate diglyceride, phosphatidyl-FIAU, or FIAU diphosphate diglyceride. In a preferred embodiment, the infection is in a human cell and the compound comprises 1-O-stearoyl-rac-3-glycerol attached to an antihepatitis B nucleoside analogue through a phosphate group.

According to yet another aspect of the invention, the lipid derivatives of nucleoside analogues are incorporated into liposomes. In a preferred embodiment, substantially all of the liposomes have a diameter less than about 100 nanometers, with a mean diameter of from about 30 to 80 nanometers. The liposomes are accordingly sized appropriately to pass through the hepatic sinusoids and to be selectively taken up by hepatocytes and targeted to the reservoir of infection. In a particularly preferred embodiment, the compound is administered parenterally to a mammal, either intravenously, subcutaneously, intramuscularly, or intraperitoneally. In an alternative embodiment, the compound is administered orally to a mammal.

The invention also provides a method for delivering an active mono-, di-, or triphosphate of a nucleotide analogue selected from the group consisting of dideoxycytidine (ddC), FIAU, FIAC, or FMAU to a cell, comprising delivering to the cell the lipid prodrug of the nucleoside analogue, and permitting the enzymatic cleavage of the prodrug to deliver the active phosphate to the cell.

The invention further provides a pharmaceutical composition, comprising an antihepatitis B compound of the invention and a pharmaceutically acceptable carrier. In one embodiment of this aspect of the invention the pharmaceutical composition further comprises a different antiviral agent.

BRIEF DESCRIPTION OF THE DRAWINGS

FIGS. 1 through 6 demonstrate the comparative levels of dideoxycytidine in specific tissues of animals treated with phosphatidyl-ddC (p-ddC) and dideoxycytidine in the corresponding tissues of those treated with free ddC (ddC) as follows:

DETAILED DESCRIPTION OF THE INVENTION

The present invention involves lipid derivatives of nucleoside analogues having an inhibiting effect on the replication of hepatitis B virus. As lipid derivatives or liponucleotides, these antiviral agents can be stably incorporated into the lipid bilayer of liposomes. These lipid derivatives can be converted into nucleoside analogue triphosphates by constituent cellular metabolic processes, and have antiviral effects in vivo and in vitro.

Related applications U.S. Ser. Nos. 07/319,485, now abandoned and 07/373,088, now U.S. Pat. No. 5,223,263 disclose lipid analogues of antiviral and antiretroviral dideoxy-, acyclic-, and deoxy-nucleosides which can be incorporated into the lipid bilayer of liposomes. These applications are hereby incorporated by reference. The drug-containing liposome particles, when introduced into an animal or human having a retroviral infection involving macrophages or monocytes, will be selectively taken up in the reservoir of infection.

Recent experiments with nucleoside analogues of this type, particularly lipid derivatives of dideoxycytidine (ddC) and azidothymidine (AZT), have shown that very large amounts of drug-containing lipid particles are taken up in the liver. Taken together with previous data which show that the lipid compounds may be metabolized in cells to antiviral metabolites, it is clear that liponucleotides of hepatitis B active nucleosides can exhibit a greatly increased potency against this infection compared to that of the free nucleosides.

Any antiviral nucleoside having the ability to inhibit the replication of hepatitis virus B virus is suitable for use in the compositions and methods of the invention. In general, the nucleoside analogues used in preparing the lipid derivatives and liposomes of the present invention will have a purine or pyrimidine base, e.g., adenine, guanine, cytosine or thymine, or an analogue thereof, attached to a pentose, such as ribose, arabinose, or a ribose or arabinose residue and/or derivative. The attachment is through the nitrogen in the 9-position of the purines or through the nitrogen in the 1-position of the pyrimidines. These nitrogens are linked by a β-N-glycosyl linkage to carbon 1 of the pentose residue.

The pentose residue may be a complete pentose, or a derivative such as a deoxypentose or dideoxypentose. In addition, the pentose residue can be a fragment of a pentose, such as a hydroxylated 2-propoxymethyl residue or a hydroxylated ethoxymethyl residue. Particular nucleoside residues having these structures include acyclovir and ganciclovir. The pentose may also have an oxygen or sulfur substitution for a carbon atom at, for example, the 3'-position of deoxyribose (BCH-189).

Preferred nucleosides are dideoxynucleosides such as 2',3'-dideoxycytidine (ddC), 2',3'-dideoxyinosine (ddI), 2',3'-dideoxyadenosine (ddA), 2',3'-dideoxythymidine (ddT), 2',3'-dideoxyguanosine (ddG); nucleoside analogues such as 9-(2-hydroxyethoxymethyl)guanine (acyclovir, ACV), E-5-(2-bromovinyl)-2'-deoxyuridine (BVdU), and 1-(2'-deoxy-2'-fluoro-1-β-arabinosyl)-5-iodocytosine (FIAC); 1-(2'-deoxy-2'-fluoro-1-β-D-arabinofuranosyl)-5-iodouracil (FIAU), 1-(2'-deoxy-2'-fluoro-1-β-D-arabinofuranosyl)-5-methyluracil (FMAU); 1-(2'-deoxy-2'-fluoro-1-β-D-arabinofuranosyl)-5-ethyluracil (FEAU); 9-β-D-arabinofuranosyladenine (ara-A), and 1-β-D-arabinofuranosylcytidine (ara-C). Also preferred are modified pyrimidine nucleosides, comprising phosphorylated forms of 2',3'-dideoxy-3'-fluorothymidine (FddThd); 2',3'-didehydro-2',3'-dideoxythymidine (ddeThd); 3'-fluoro-5-methyl-deoxycytidine (FddMeCyt); 3'-chloro-5-methyl-deoxycytidine (ClddMeCyt); and 3'-amino-5-methyl-deoxycytidine (AddMeCyt); as well as isoddA, isoddG, 2-CDG, and BVara-U. Particularly preferred nucleosides are 2',3'-dideoxycytidine (ddC) and 9-β-D-arabinofuranosyladenine (ara-A).

Any lipid derivative of the nucleoside analogues disclosed, having an activity against hepatitis B, is within the scope of the invention. The lipid groups are preferably attached to the nucleoside analogues through a phosphate link between the nucleoside analogue and the lipid. The phosphate groups may be either mono-, di-, or triphosphate groups and are generally connected to the 5' carbon of the pentoses in the compounds of the present invention; however, compounds wherein the phosphate groups are attached to the 3' hydroxyl group of the pentose are within the invention if they possess antihepatitis B activity. Where lipids are linked directly to pentose groups, those linkages may also be made either through the 3', or preferably through the 5', pentose carbon.

The lipids to which the antiviral nucleosides are bound have hydrophobic acyl groups capable of anchoring the liponucleoside in the lipid bilayer. Suitable lipids are, for example, mono- or diacylglycerides, sphingosine and dihydrosphingosine, and long chain fatty acids or alcohols. Other suitable lipids are those having novel structures, for example, ether-linked lipids such as batyl alcohol, 1-O-stearoyl-rac-3-glycerol, or those comprising ammonium groups, for example, D,L-2,3-distearoyloxypropyl (dimethyl)-β-hydroxyethyl ammonium (6). Liponucleotides may include more than one lipid moiety attached to the phosphate linker.

The aliphatic groups of the lipid moieties preferably have chain lengths of two to twenty-four carbon atoms and can be saturated or unsaturated with up to six double bonds. The aliphatic groups may be attached to the glycerol moiety by acyl ester, ether, thioester, thioether, or vinyl ether bonds.

Structures of several groups of lipid derivatives of nucleoside analogues, comprising phosphatidylnucleosides, nucleoside diphosphate diglycerides, nucleoside acyl phosphates, and ceramide phosphonucleosides, are disclosed in copending application Ser. No. 07/373,088, now U.S. Pat. No. 5,223,263.

Preferred antihepatitis liponucleotides of the invention are phosphatidyl-dideoxyadenosines (p-ddA), phosphatidyl-dideoxycytidines (p-ddC), phosphatidyl-dideoxyguanosines (p-ddG), phosphatidyl-dideoxyinosines (p-ddI), phosphatidyl-dideoxythymidines (p-ddT), phosphatidyl-9-(2-hydroxymethyl)-guanosines (p-ACV), phosphatidyl-1-(2'-deoxy-2'-fluoro-1-β-arabinosyl)-5-iodocytosines (p-FIAC), phosphatidyl-1-(2'-deoxy-2'-fluoro-1-β-arabinosyl)-5-iodouracils (p-FIAU), phosphatidyl-9-β-D-arabinofuranosyladenines (p-ara-A), dideoxyadenosine diphosphate diglycerides (ddADP-dg), dideoxy-cytidine diphosphate diglycerides (ddC-DP-dg), dideoxycytidine diphosphate bis(diacylglycerol), dideoxycytidine diphosphate D,L-2,2-diacyloxypropyl-(dimethyl)-β-hydroxyethyl ammonium, dideoxyguanosine diphosphate diglycerides (ddGDP-dg), dideoxyinosine diphosphate diglycerides (ddIDP-dg), dideoxythymidine diphosphate diglycerides (ddTDP-dg), 9-(2-hydroxymethyl)guanosinediphosphate diglycerides (ACVDP-dg), 1-(2'-deoxy-2'-fluoro-1-β-arabinosyl)-5-iodocytosine diphosphate diglycerides (FIACDP-dg), 1-(2'-deoxy-2'-fluoro-1-β-arabinosyl)-5-iodouracil diphosphate diglycerides (FIAUDP-dg), and 9-β-D-arabinofuranosyladenine diphosphate diglycerides (ara-ADP-dg).

Synthesis of Antiviral Liponucleotides

The compounds of the invention are formed according to synthetic procedures which couple a phospholipid to a nucleoside analogue or which couple a phospholipid to a nucleoside analogue monophosphate or diphosphate, wherein the phosphate group of the nucleoside is located on the ribose group of the nucleoside, at either the 3' or preferably the 5' location. The synthesis can be carried out according to general methods applicable to all lipids and all antiviral nucleosides described, as in Examples 1 through 7 of copending application U.S. Ser. No. 07/373,088, now U.S. Pat. No. 5,223,263 but preferably according to the methods of synthesis described in Examples 1–3.

Lipids comprising fatty acids, fatty alcohols, glycerides, and phospholipids may be purchased from commercial suppliers (Avanti Polar Lipids, Inc., Pelham, Ala. 35124) or may be synthesized according to known methods. Antiviral nucleoside analogues are available from Aldrich, Milwaukee, Wis. or from Sigma, St. Louis, Mo.

It is important that all traces of water be removed from the reactants in order for the coupling reactions to proceed. Therefore, the lipids are first either freeze-dried by solvent evaporation under vacuum, or in a vacuum oven over $P_2O_5$. The reactions are also carried out under an inert gas, such as, for example, argon, A.

Liponucleotides comprising a mono-, di-, or triphosphate link between an antiviral nucleoside analogue and the lipid group may be prepared from phospholipids, phosphorylated nucleoside analogues, or both.

Suitable phospholipids comprise phosphoglycerides, sphingolipids, or acyl phosphates. Phosphorylated nucleoside analogues are known. The dideoxynucleoside analogue is phosphorylated according to conventional procedures such as the phosphorous oxychloride method of Yoshikawa et al. (7,8) or Toorchen and Topal (9). The preferred modified analogue is the 5'-monophosphate. Lipids suitable for coupling to nucleosides, comprising primarily long chain fatty acids or alcohols, monoglycerides or diglycerides, sphingosines and other lipid species described below, may be phosphorylated by treatment with appropriate agents, for example using phenyl phosphorodichloridate according to the procedure of Brown (10), by treatment with phosphorus oxychloride, or by other known phosphorylation procedures.

In the first type of synthesis, a phospholipid, such as, for example, a phosphatidic acid, is coupled to a selected nucleoside analogue at either the 3' or 5' hydroxyl by means of a coupling agent, such as, for example, 2,4,6-triisopropylbenzenesulfonyl chloride in the presence of a basic catalyst, for example, anhydrous pyridine, at room temperature, as in Example 1D. Other coupling agents, such as dicyclohexyl-carbodiimide can be used.

Lipid derivatives can also be synthesized by coupling a phosphatidic acid to an antiviral nucleoside monophosphate through a pyrophosphate bond. In this procedure, the nucleoside monophosphate or diphosphate is converted to a derivative having a leaving group, for example, morpholine, attached to the terminal phosphate group, according to the procedure of Agranoff and Suomi (11). A coupling of the phosphatidic acid and the nucleoside phosphate morpholidate occurs on treatment of a dry mixture of the two reactants with a basic catalyst, such as anhydrous pyridine, at room temperature.

Alternatively, the phosphatidic acid can be converted to a derivative having a leaving group, for example, morpholine, as described in Example 2D and 3A. The coupling of the phosphatidic acid morpholidate and the nucleoside phosphate occurs on treatment of the mixture with a basic catalyst, Example 2E and 3C. This alternative synthetic method is the subject of a U.S. patent application Ser. No. 07/706,873, filed May 29, 1991, abandoned in favor of U.S. Ser. No. 08/251,018, filed May 31, 1994.

The synthetic reactions are followed using thin layer chromatography (TLC) with appropriate solvents. When the reaction, as determined by TLC, is complete, the product is extracted with an organic solvent and purified by chromatography on a support suitable for lipid separation, for example, silicic acid.

The synthesis of products comprising adenine or cytidine having reactive amino groups may be facilitated by blocking those groups with acetate before the coupling reaction by treatment with acetic anhydride; after the chromatography of the final product, the amino groups are unblocked using dilute ammonium hydroxide.

In any of the lipid derivatives of the invention, the nucleoside may be any antiviral nucleoside having antihepatitis activity; $R_{1-2}$ (as well as $R_{3-4}$ for the bis(diacylglycero) phosphate species) may be any saturated or unsaturated fatty acid having from 2 to 24 carbon atoms. Polyunsaturated, hydroxy, branched chain, and cyclopropane fatty acids are also possible. The stereochemistry of the glycerol moieties can include sn-1 or sn-3 phosphoester bonds or racemic mixtures thereof. There may be 1 or 2, (as well as 3, or 4 for the bis(diacylglycero) phosphate species) acyl ester groups, or alkyl ether or vinyl ether groups, as required.

A variety of other phospholipids may be linked to nucleosides, including, but not limited to phosphatidylglycerol, phosphatidylinositol, or any other phospholipid wherein the head group contains an available linking hydroxyl group, in either a natural polyhydroxyl alcohol such as inositol, or one in which it has been substituted by another polyhydroxy alcohol or by a carbohydrate, such as a sugar, again either natural or synthetic. In this case the nucleoside phosphate will be added by esterification to one or more of the hydroxyls of the alcohol or carbohydrate. Other glycolipids may also serve as the ligand to which the phosphate group of the nucleotide is attached by means of esterification to a glycolipid hydroxyl group. Other glycolipids, whether or not phospholipids, such as selected cerebrosides or gangliosides, either natural or synthetic, having suitable hydrophobic properties may also be advantageously used. These may also be linked to nucleotides by similar esterification of carbohydrate hydroxyl groups.

Furthermore, antiviral nucleosides can be linked to the phosphate groups of the phosphatidylinositol mono-, di- and triphosphates, or to the phosphate-substituted carbohydrate moieties of phospholipids or glycolipids, either natural or synthetic.

Phosphatidylserine may be linked to nucleoside analogues directly by esterification of its carboxyl group with the 5'-hydroxyl of the nucleoside ribose group. Synthetic phospholipids which are similar in structure to phosphatidylserine, in the presence of a carboxyl group in the polar headgroup, may be linked in a similar way.

Phospholipids having alkyl chains attached by ether or vinyl ether bonds may also be used to prepare nucleotide derivatives. Suitable phospholipids for this purpose comprise naturally occurring acetal phosphatides, or plasmalogens, comprising a long chain fatty acid group present in an unsaturated vinyl ether linkage. Alternatively, analogues of 1-O-alkyl glycerol or 2-O-alkyl glycerol may be prepared synthetically, and linked to a selected nucleotide. Derivatives of 1-O-alkyl-glycero-3-phospho-5'-dideoxycytidine are preferred, and may be prepared by condensing ddC monophosphate with various analogues of 1-O-alkyl-glycerol having an alkyl group of 2 to 24 carbon chain length at the 1 position of glycerol. The 1-O-alkyl group may consist of a saturated or unsaturated aliphatic group having a chain length of 2 to 24 carbon atoms. The 1-O-alkyl glycerol residue may be racemic or stereospecific. This compound may be acylated with fatty acid chlorides or anhydrides resulting in the synthesis of 1-O-alkyl, 2-acyl-glycero-3-phospho-5'-dideoxycytidine. Similarly, by using a large excess of dideoxycytidine monophosphate, the 1-O-alkyl, 2,3-bis(phospho-5'-2',3'-deoxycytidine)glycerol analogues may be synthesized. These derivatives have the general structure:

Where $R^1$ is an unsaturated or saturated alkyl chain 1 to 23 carbon atoms in length in ether or vinyl ether linkage. $R^2$ is OH or a saturated or unsaturated fatty acid ester of 2 to 24 carbon atoms. An ether or vinyl ether link at $R^2$ is also possible. The group at position 1 of glycerol may also be OH if $R^2$ is the ether linked alkyl chain. N is any antiviral nucleoside having activity against hepatitis B, linked in a 5' phosphodiester link, and A is a chalcogen (O, C or S).

Although phosphorylated antiviral nucleosides (nucleotides) are preferred embodiments of the present invention, it is possible to utilize non-phosphorus containing lipid derivatives of nucleoside analogues if it is not necessary to provide the infected cell with the nucleoside phosphate in order to achieve an antiviral effect through the processes of cellular metabolism. Some examples of compounds of this type would have fatty acids esterified, or present in alkyl linkage, directly to the 5'-hydroxyl of the nucleoside according to the synthetic method of the invention.

Alternatively, a "spacer" molecule having, for example, carboxyl groups at either end and 0 to 10 $CH_2$ groups in the center, could be esterified to the 5'-hydroxyl of the antiviral nucleoside. The other carboxyl of the "spacer" may be esterified to the free hydroxyl of diacylglycerol or any other lipid having an available hydroxyl function. Other linking ("spacer") groups with suitable functional groups at the ends may also be used to link the diglyceride or other suitable lipid group to the nucleoside, by chemical methods well known to those skilled in the art.

Preparation of Liposomes comprising Lipid Derivatives of Antihepatitis B Nucleosides According to one aspect of the present invention, the antiviral nucleoside derivatives noted above are incorporated in liposomes in order to direct these compounds to cells which take up the liposomal composition.

The incorporation can be carried out according to well known liposome preparation procedures, such as sonication, or by extrusion. Suitable conventional methods of liposome preparation also include, but are not limited to, those disclosed by Bangham, et al. (13), Olson, et al. (14), Szoka and Papahadjapoulos (15), Mayhew, et al. (16), Kim, et al. (17), Mayer, et al. (18) and Fukunaga, et al. (19). Liposomes suitable for use in the methods of the invention may also be prepared by microfluidization, using, for example, a commercial device (MICROFLUIDIZER® microemulsifer, Newton, Mass.). Ligands may also be incorporated to further focus the specificity of the liposomes.

The size of liposomes is related to achieving effective uptake of antihepatitis B nucleoside analogues into the HBV-infected parenchymal cells of the liver, the hepatocytes, in the treatment of hepatitis B infection. If one makes liposomes containing a lipid derivative of a nucleotide analogue and having a diameter of less than 100 nanometers, the drug may be targeted in a highly efficient manner to these parenchymal cells. The intrahepatic distribution of systemically administered liposomes has been demonstrated by the group of G. Scherphof in Holland using liposome-encapsulated radioactive inulin as a marker (12). According to these studies, the uptake of liposomes into parenchymal cells appears to be limited by the morphology of the hepatic sinusoids wherein fenestrations of about 100 nm in diameter deny efficient access of particles larger than 100 nm to the underlying hepatocytes. Liposomes of relatively large size are preferentially taken up by the resident macrophages of liver, the Kupffer cells (20, 21). Accordingly, liposomes containing anti-hepatitis nucleoside analogues should be less than 200 nanometers in diameter, preferably less than 100 nanometers in diameter, and in the range of about 30 to 80 nanometers in diameter. In view of the Sherphof findings, liposomes containing the antihepatitis B nucleotide of a diameter less than 100 nanometers can be expected to target drugs with improved efficiency to the hepatic parenchymal cells to achieve a very large and effective uptake of drug by the liver.

Sizing of liposome preparations to a selected diameter is accomplished by extrusion through a NUCLEOPORE® filter of appropriate pore size, as indicated in Example 4, by passage through a ceramic filter as disclosed in U.S. Pat. No. 4,737,323 to Martin, or preferably by processing in a microemulsifier apparatus (MICROFLUIDIZER® microemulsifer, Biotechnology Development Corporation, Newton, Mass.), as described in Example 6.

Liposomes can be made from the lipid derivatives of nucleoside analogues, preferably in combination with any of the conventional synthetic or natural phospholipid liposome materials including phospholipids from natural sources such as egg, plant or animal sources such as phosphatidylcholines, phosphatidylethanolamines, phosphatidylglycerols, sphingomyelins, phosphatidylserines, or phosphatidylinositols. Synthetic phospholipids that may also be used, include, but are not limited to, dimyristoylphosphatidylcholine, dioleoylphosphatidylcholine, dipalmitoylphosphatidylcholine and distearoylphosphatidylcholine, and the corresponding synthetic phosphatidylethanolamines and phosphatidylglycerols. Other additives such as cholesterol or other sterols, cholesterol hemisuccinate, glycolipids, cerebrosides, fatty acids, gangliosides, sphingolipids, 1,2-bis(oleoyloxy)-3-(trimethyl ammonio)propane (DOTAP), N-[1-(2,3-dioleoyl) propyl]-N,N,N-trimethylammonium (chloride) (DOTMA), D,L,-2,3-distearoyloxypropyl(dimethyl)-β-hydroxyethyl ammonium (acetate), 1,2-dioleoyl-3-dimethylaminopropyl-β-hydroxyethylammonium acetate (DORI diester), 1, 2-O-dioleyl-3-dimethylaminopropyl-β-hydroxyethylammonium acetate (DORI diether), (DORI ester/ethers), glucopsychosine, or psychosine can also be added, as is conventionally known. The relative amounts of phospholipid and additives used in the liposomes may be varied if desired. The preferred ranges are from about 80 to 95 mole percent phospholipid and 5 to 20 mole percent psychosine or other additive. Cholesterol, cholesterol hemisuccinate, fatty acids or DOTAP may be used in amounts ranging from 0 to 50 mole percent. The amounts of antiviral nucleoside analogue incorporated into the lipid layer of liposomes can be varied with the concentration of their lipids ranging from about 0.01 to about 90 mole percent, preferably up to about 40 or 60 mole percent.

Using conventional methods to entrap active compound entraps approximately 20 to 50% of the material present in solution; thus, approximately 50 to 80% of the active compound is wasted. In contrast, where a lipid derivative of a nucleoside analogue is incorporated into the lipids, virtually all of the nucleoside analogue is incorporated into the liposome, and virtually none of the active compound is wasted.

The lipid derivatives of the invention can also be prepared for therapeutic use as emulsions or microemulsions, free from emulsifying agents, wherein the formulations described above are present as dispersed phase droplets of very small diameters in an aqueous medium. See, for example, the apparatus for forming such emulsions, U.S. Pat. No. 4,533,254 to Cook et al., disclosing the formation of such microemulsions wherein the dispersed phase droplets range from about 0.010 μm to about 0.2 μm in diameter.

Therapeutic Uses of Lipid Derivatives of Antihepatitis Nucleosides

The liposomally incorporated phosphorylated nucleoside analogue is administered to patients by any of the known procedures utilized for administering liposomes. The liposomes can be administered intravenously, intraperitoneally, intramuscularly, or subcutaneously as a buffered aqueous solution; alternatively, they can be administered orally in liquid or solid formulations. Any pharmaceutically acceptable aqueous buffer or other vehicle may be utilized so long as it does not destroy the liposome structure or the activity of the antiviral nucleoside analogue. Examples of suitable aqueous buffers are 150 Mm Nacl containing 5 Mm sodium phosphate with a pH of about 7.4, or any other physiological buffered salt solutions.

The dosage for a mammal, including a human, may vary depending upon the extent and severity of the infection and the activity of the administered compound. Dosage levels for antiviral nucleoside analogues are well established. Dosage levels of lipid derivatives of nucleoside analogues should be such that about 0.001 mg/kilogram to 1000 mg/kilogram is administered to the patient on a daily basis and more preferably from about 0.05 mg/kilogram to about 100 mg/kilogram, measured as the nucleoside analogue portion of the liponucleotide.

The derivatives described have several unique and novel advantages over the water soluble dideoxynucleoside phosphates described in an earlier copending application, Ser. No. 07/099,755, now abandoned. First, they can be formulated more efficiently. Liposomes comprising lipid derivatives of nucleoside analogues have much higher ratios of drug to lipid because they are incorporated into the wall of the liposome instead of being located in the aqueous core compartment. Secondly, the liposomes containing the lipophilic dideoxynucleoside derivatives noted above do not leak during storage, providing improved product stability. Furthermore, these compositions may be lyophilized, stored dry at room temperature, and reconstituted for use, providing improved shelf life. They also permit efficient incorporation of antiviral compounds into liposomal formulations without significant waste of active compound. They also provide therapeutic advantages. Stability of the liposomally incorporated agent causes a larger percentage of the administered antiviral nucleoside to reach the intended target, while the amount being taken up by cells in general is minimal, thereby decreasing the toxic side effects of the nucleosides. The toxic side effects of the nucleosides may be further reduced by targeting the liposomes in which they are contained to actual or potential sites of infection by incorporating ligands specifically binding thereto into the liposomes.

Finally, the compounds noted above have been constructed in a novel way which may give rise to phosphorylated dideoxynucleosides or other antiviral nucleosides upon further-cellular metabolism. This improves their antiviral effect in cells which are known to be resistant to the effects of the free antiviral compounds. Indeed, use of the present invention may provide a method for delivering biologically active phosphorylated nucleosides to the interior of a cell. The compounds of the present invention are thus precursors or prodrugs of phosphorylated nucleoside analogues.

Lipid derivatives of antiviral agents have a prolonged antiviral effect as compared to the lipid-free agents; therefore they provide therapeutic advantages as medicaments even when not incorporated into liposomes. Nonliposomal lipid derivatives of antiviral nucleoside analogues may be applied to the skin or mucosa or into the interior of the body, for example orally, intratracheally or otherwise by the pulmonary route, enterally, rectally, nasally, vaginally, lingually, intravenously, intra-arterially, intramuscularly, intraperitoneally, intradermally, or subcutaneously. The present pharmaceutical preparations can contain the active agent alone, or can contain further pharmaceutically valuable substances. They can further comprise a pharmaceutically acceptable carrier, including bioerodible or other time release carriers.

Pharmaceutical preparations containing lipid derivatives of antiviral nucleosides are produced by conventional dissolving and lyophilizing processes to contain from approximately 0.01% to 100%, preferably from approximately 0.1% to 50%, weight percent, of the active ingredient. They can be prepared as ointments, salves, tablets, capsules, powders or sprays, together with effective excipients, vehicles, diluents, fragrances or flavor to make palatable or pleasing to use.

Oral administration of liponucleotide analogues may be advantageous in assuring effective liver uptake. Formulations for oral ingestion are in the form of tablets, capsules, pills, ampoules of powdered active agent, or oily or aqueous suspensions or solutions. Tablets or other non-liquid oral compositions may contain acceptable excipients, known to the art for the manufacture of pharmaceutical compositions, comprising diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract.

Aqueous suspensions may contain the active ingredient in admixture with pharmacologically acceptable excipients, comprising suspending agents, such as methyl cellulose; and wetting agents, such as lecithin or long-chain fatty alcohols. The the aqueous suspensions may also contain preservatives, coloring agents, flavoring agents and sweetening agents in accordance with industry standards. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure.

The therapeutically effective amount of the lipid derivatives is determined by reference to the recommended dosages of the active antiviral nucleotide, bearing in mind that, in selecting the appropriate dosage in any specific case, consideration must be given to the patient's weight, general health, metabolism, age and other factors which influence response to the drug. The parenteral dosage will be appropriately ¾ to ¹⁄₁₀ of the oral dose, and may be given by intravenous, subcutaneous, intramuscular, or intraperitoneal route.

The efficacy of the antihepatitis liponucleotides of the invention was demonstrated in tests carried out both in vitro and in vivo. The in vivo tests were carried out as described in Example 5 and the pharmacokinetic results are shown in FIGS. 1–6. The efficacy was evaluated by noting the area under the curve (AUC) of dose level v. time. Notably the AUC of phosphatidyl-ddC in liver was 42 times greater than that of free ddC, demonstrating clearly the anticipated targeting feature of this novel liponucleotide. At the same time, the AUC in sciatic nerve and brain, the sites of toxic damage for ddC, showed effective tissue levels not substantially greater than that for the free drug. Based on this data, it appears that targeted anti-HBV analogues such as phosphatidyl-ddC may be able to increase efficacy in treating hepatitis B while decreasing neurotoxicity which is the major clinical problem with ddC.

Lipid derivatives of antihepatitis nucleosides are effective against HBV in cells in culture. In vitro tests using 3 different lipid derivatives of FIAC and 3 corresponding lipid derivatives of FIAU were carried out in hepG2.2.15 HBV-infected cells as described in Example 4, Section B and Table 1. The data shows that the FIAC and FIAU liponucleotides have substantial activity in vitro. The lipid control, dioleoylphosphatidylcholine (DOPC; 40W and 40X) is without activity. In vitro tests using a dioleoylglycero-3-phospho-5'-(2',3'-dideoxycytidine) were carried out in hepG2.2.15 HBV-infected cells as described in Example 4, Section C, and Table 2. Again, both ddC and corresponding liponucleotides have substantial activity against the HBV virus in cells in culture, while the lipid control, dioleoylphosphatidylcholine (DOPC) is without activity.

Lipid derivatives of antiviral nucleotides demonstrate an ability to access specialized cells and tissues, particularly those of the liver, preferentially, and in this way to target the reservoirs of hepatitis B infection. The data of Example 5, as represented in FIGS. 1a–1f, demontrates this targeting advantage in the enhanced levels of ddC delivered to and maintained in these cells and tissues by lipid derivatives of ddC and the corresponding reduced levels in tissues subject to the toxic effects of ddC.

Based on the demonstrated properties, the lipid derivatives of the invention offer an effective therapeutic agent for the treatment of hepatitis B infections. No generally effective therapy now exists for this disease. Clinical experience with present therapies indicates that a general antiviral agent, Interferon alpha, may be effective in only some selected cases, and the toxic effects of antiviral dideoxynucleosides, such as dideoxycytidine, known to have antihepatitis activity, may be a limiting factor in using these agents in therapeutic regimens.

Figure 4:
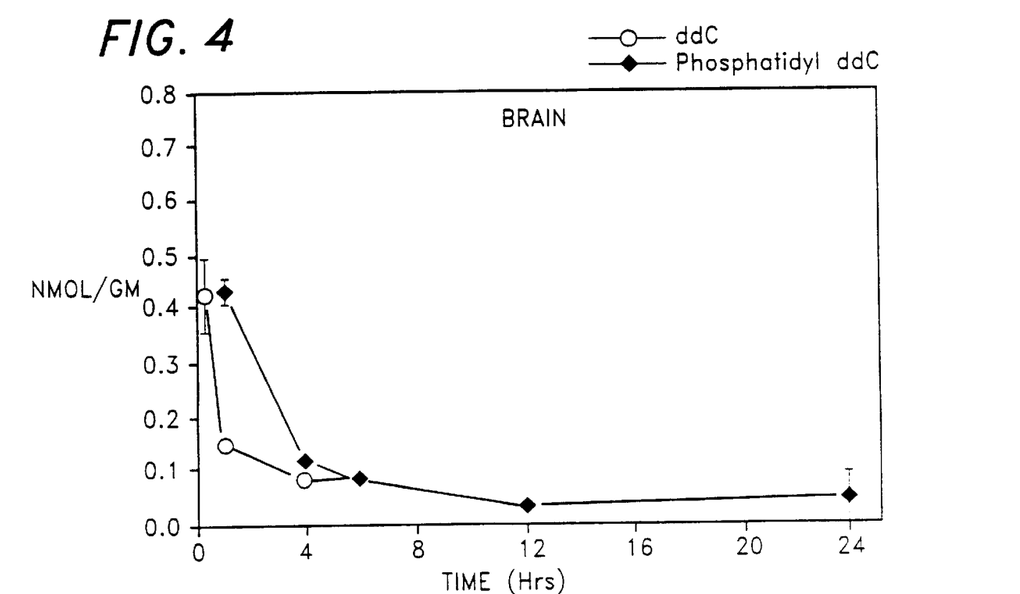
FIG. 4 is a graph showing the comparative levels of ddC in brain.
Figure 5:
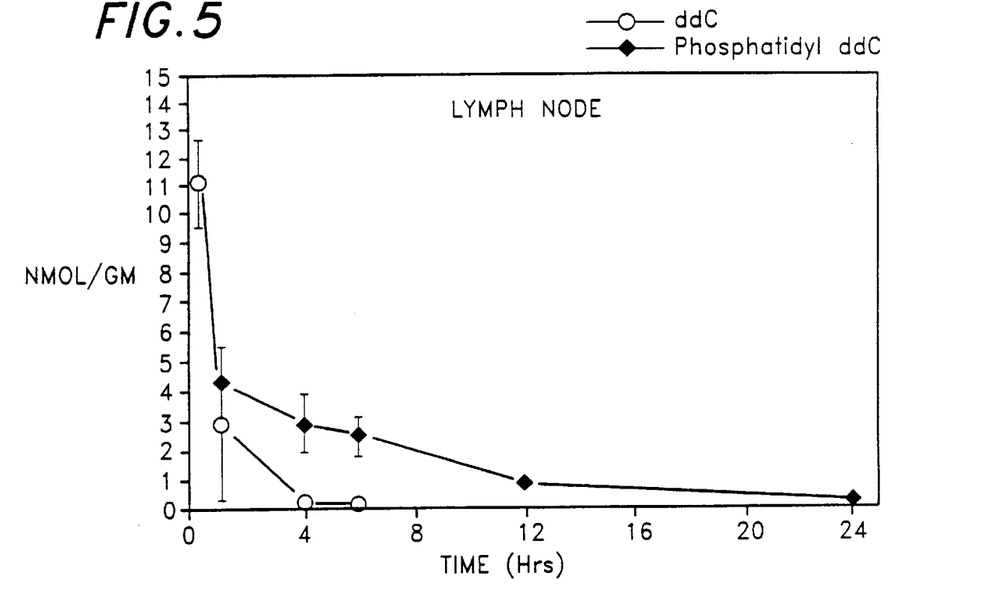
FIG. 5 is a graph showing the comparative levels of ddC in lymph node.
Figure 6:
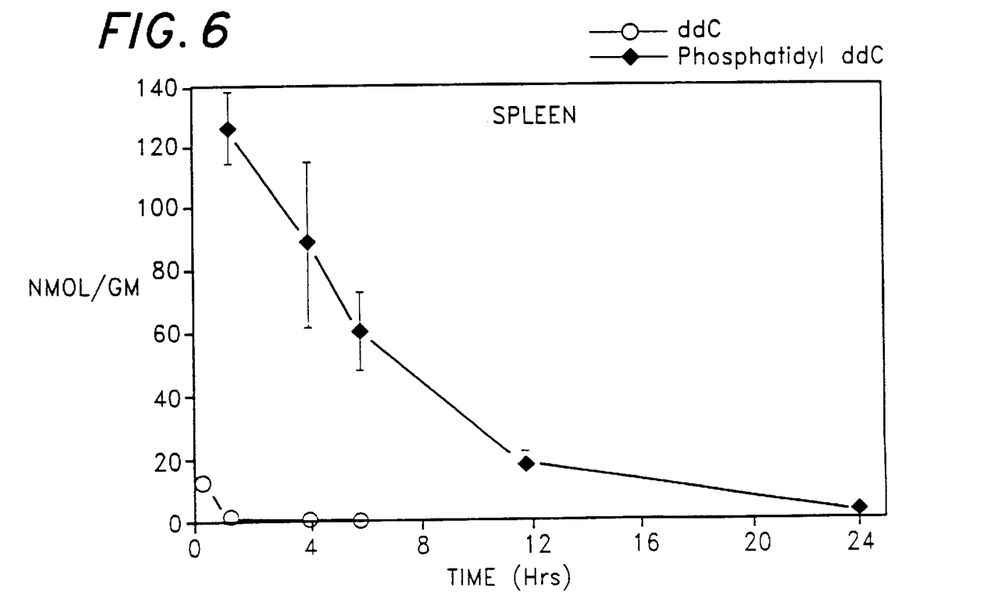
FIG. 6 is a graph showing the comparative levels of ddC in spleen.

Based on the information gained from the inhibition of DNA production of HBV-infected cells in tissue culture, and the targeted delivery in mice provided by liposomal lipid derivatives of anti-HBV agents, and taken together with previous studies with retroviral-infected cells showing that liponucleotides are converted to antiviral metabolites intracellularly (See, for example, Experiment H637-1b and FIG. 4 of copending application 07/373,088, now U.S. Pat. No. 5,223,263), it is possible to formulate a strategy for similar inhibition of HBV in HBV-infected patients, as well as in individuals harboring the virus but not manifesting symptoms of the disease.

In an HBV-infected patient, the virus proliferates within infected cells, and in order to treat the disease and prevent the replication of viral DNA, the antiviral agent must be administered to the patient in a manner capable of introducing the agent initially into the bloodstream and ultimately into the cells. In consideration of this data and the finding that appropriate sizing of liposomes achieves highly efficient uptake into a site of hepatitis B infection in the liver, it is anticipated that the lipid derivatives of any antihepatitis B nucleoside, incorporated into liposomes of effective small diameter, will be effective in vivo at lower doses with anticipated lower toxicity.

A more complete understanding of the invention can be obtained by referring to the following illustrative examples, which are not intended, however, to unduly limit the invention.

EXAMPLE 1

Synthesis of 1,2-Dimyristoylglycerophospho-5'-(2',3'-dideoxy)cytidine

A. Materials

Phosphatidic acids, for example, dilauroyl, dimyristoyl, and dipalmitoyl phosphatidic acids, were obtained as disodium salts from Avanti Polar lipids (Pelham, Ala., USA). Dowex 50 W (50×2–200, 100–200 mesh), and 2',3'-dideoxycytidine were products from Sigma Chemical Co. (St. Louis, Mo., USA). Morpholine, dicyclohexylcarbodiimide (DCC) and tertiary butyl alcohol (2-methyl-2-propanol, tBuOH) were the highest grade available from Aldrich Chemical Co. (Milwaukee, Wis., USA). alcohol (2-methyl-2-propanol, tBuOH) were the highest grade available from Aldrich Chemical Co. (Milwaukee, Wis., USA).

B. Conversion of Phosphatidic Acid Salts To The Free-Acid Form

Phosphatidic acids, disodium salts, were acidified by application of an extraction procedure according to Bligh and Dyer, Can. J. Biochem. 37, 911–917 (1959). Thus, 1 mmol of lipid was dissolved in a homogenous mixture of 100 ml $CHCl_3$, 200 ml MeOH, 100 ml 0.1M HCl and stirred at room temperature for one hour. Then 100 ml $H_2O$ and 100 ml $CHCl_3$ were added, the separated $CHCl_3$ layer was isolated and the aqueous phase was extracted twice with 200 ml $CHCl_3$. The combined $CHCl_3$ extracts were evaporated to dryness and lyophilized. Yield: 95–100% phosphatidate as the free acid.

B: Preparation of 4-acetyl-2'3'-dideoxycytidine

To a stirred, refluxing solution of 2'-3'-dideoxycytidine (ddC:400 mg, 1.89 mmol) in anhydrous ethanol (35 ml, dried first with Lindy type 4×molecular sieve, and twice distilled over magnesium turnings) was added acetic anhydride (0.4 ml, 5.4 mmol). During the course of a 3 hour refluxing period, four more additional 0.4 ml portions of acetic anhydride were added at 30 minute intervals. The reaction was followed by thin layer chromatography (silica gel F254, Kodak Chromagram, developed with 10% methanol in chloroform). After the final addition, the solution was refluxed for 1 more hour. The reaction mixture was cooled and solvent was evaporated under diminished pressure. The residue was redissolved in 8% methanol in chloroform (5 ml) and chromatographed on a silica gel column (2.2 cm×30 cm, Kieselgel 60, 70–230 mesh, EM Science, 45 g). The column was eluted with 8% methanol in chloroform to yield pure 4-acetyl-2'3'-dideoxycytidine (ddC-OAC) in 80% yield.

D: Coupling reaction

A day before the coupling reaction, DMPA-H (prepared as described in B. above, 250 mg, 0.42 mmol) was dissolved in cyclohexane (10 ml) in a round-bottom flask (50 ml) and the solvent evaporated under reduced pressure at room temperature. This process was repeated four more times and DMPA-H further dried in a vacuum oven at room temperature overnight over $P_2O_5$. Under argon, to the 50 ml round-bottom flask containing dried DMPA-H was added dried ddC-OAC (85 mg, 0.33 mmol, dried over $P_2O_5$ under vacuum overnight), and 2,4,6-triisopropyl-benzenesulfonyl chloride (TPS), (315 mg, 1.04 mmol), and anhydrous pyridine (2 ml) via syringe to obtain a clear solution. The reaction mixture was stirred at room temperature for 18 hours. (The reaction was followed by thin layer chromatography). Water (1 ml) was added to the mixture to destroy excess catalyst. The solvent was evaporated under reduced pressure to yield a yellow gum which was redissolved in a small volume of methanol in chloroform (1:9 by volume) and applied to a column of silica gel (45 g, Kieselgel 60, EM Science). The column was topped with a small amount of sand (500 mg) to prevent the sample from floating during elution. The column was eluted with 8% methanol in chloroform (1.5 L). After a forerun (rejected), then dimyristoylphosphatidyl-5'-(2'3'-dideoxy)cytidine (DMPA-ddC) was obtained. The fractions containing the product were combined and the solvent was evaporated under reduced pressure. The residue was further dried with cyclohexane to yield pure DMPA-ddC-OAC (210 mg, 0.21 mmol, in 70% yield). $R_f$ 0.40 (silica gel GF, 20×20 cm, Analtech, chloroform:methanol:water:ammonia 80:20:1:1 by volume).

E: Deblocking with 9N NH4OH ddC-OAC-DMPA (40 mg, 0.04 mmol) was dissolved in chloroform:methanol (1:1,2 ml), and 9N $NH_4OH$ (10 drops) was added at once. The solution was stirred at room temperature for 15 minutes and was then quickly neutralized with glacial acetic acid to pH 7. The neutralized solution was evaporated to dryness overnight under reduced pressure to yield dimyristoylphosphatidyl 5'(2'3'-dideoxy)cytidine (DMPA-ddC, 35 mg, 0.037 mmol). Melting point: DMPA-ddC decomposed at 240° C. On thin layer chromatography on silica gel GF plates, the Rf values were: 0.11 (chloroform:methanol:water:ammonia 80:20:1:1); 0.38 (chloroform:methanol:ammonia:water 70:30:3:2); 0.15 (chloroform:methanol:water 65:25:4); UV absorption maximum 273 nm (e 5,800).

NMR: (CDCL3) d 0.86 (6H, bt, acyl CH3), 1.24 (40H, bs, acyl CH2), 1.57 (4H, m, β acyl CH2), 2.28 (4H, m, α acyl CH2), 3.36 (2H, m, ribose 5'H), 3.94 (2H, bs, sn-3 $CH_2$ glycerol), 4.19 (1H, m, sn-1 $CH_2$ glycerol), 4.29 (1H, m, sn-1 $CH_2$ glycerol), 4.40 (1H, bs, ribose 4'H), 5.19 (1H, m, sn-2 CH glycerol), 5.89 (1H, m, thymine 5-H), 7.44 (1H, bs, thymine NH3), 7.94 (1H, bs, thymine $NH_2$). The peak area ratio of phosphatidic acid to 2'3'-dideoxycytidine is 1.

EXAMPLE 1a: 1,2-dilauroylglycerophospho-5'-(2',3'-dideoxycytidine), DLP-ddC; EXAMPLE 1c: 1,2-dipalmitoylglycerophospho-5'-(2',3'-dideoxycytidine), DPM-ddC; EXAMPLE 1d: 1,2-stearoylglycerophospho-5'-(2',3'-dideoxycytidine), DSP-ddC;

EXAMPLE 1e: 1,2-dilauroylglycerophospho-5'-(2'-deoxy-2'-fluoro-1-β-arabinosyl)-5-iodocytosine, DLP-FIAC; EXAMPLE 1f: 1,2-dimyristoylglycerophospho-5'-(2'-deoxy-2'-fluoro-1-β-arabinosyl)-5-iodocytosine, DMP-FIAC; EXAMPLE 1g: 1,2-dipalmitoylglycerophospho-5'-(2'-deoxy-2'-fluoro-1-β-arabinosyl)-5-iodocytosine, DPM-FIAC; EXAMPLE 1h: 1,2-stearoylglycerophospho-5'-(2'-deoxy-2'-fluoro-1-β-arabinosyl)-5-iodocytosine, DSP-FIAC;

EXAMPLE 1i: 1,2-dilauroylglycerophospho-5'- (2'-deoxy-2'-fluoro-1-β-arabinosyl)-5-iodouracil, DLP-FIAU; EXAMPLE 1j: 1,2-dimyristoylglycerophospho-5'-(2'-deoxy-2'-fluoro-1-β-arabinosyl)-5-iodouracil, DMP-FIAU; EXAMPLE 1k: 1,2-dipalmitoylglycerophospho-5'-(2'-deoxy-2'-fluoro-1-β-arabinosyl)-5-iodouracil, DPM-FIAU; and EXAMPLE 1l: 1,2-stearoylglycerophospho-5'-(2'-deoxy-2'-fluoro-1-β-arabinosyl)-5-iodouracil, DSP-FIAU are prepared according to the above method except for using an appropriate species of phosphatidic acid in the coupling step. Lipid derivatives of FIAC and FIAU are prepared using dicyclohexylcarbodiimide (DCC) instead of (TPS) as a coupling agent, and using the same molar ratio of reactant and coupling agent. All the compounds of Examples 1a through 1l are worked up and purified in the manner described.

EXAMPLE 2

Synthesis of 1-(2'-DEOXY-2'-FLUORO-β-D-ARABINOFURANOSYL)-5-IODOURACIL-5'-DIPHOSPHATE-sn-3-(1,2-DIPALMITOYL) GLYCEROL (FIAU-DP-DPG)

A: Materials

Phosphorus oxychloride, phosphorus trimethylphosphate, silica 60 F 254 HPTLC plates (10×20 cm), silica 60 F254 aluminum plates (5×10 cm), HPLC grade solvents (Lichrosolv) and all other chemicals were from Merck (Darmstadt, FRG), unless stated otherwise.

B. Phosphorylation of Nucleosides

The phosphorylation of unprotected nucleosides with $POCl_3$ in $(CH_3O)_3PO$ was essentially performed as described by Yoshikawa, et al., *Tetrahedron Lett.* 50, 5065–5068 (1967); and Yoshikawa, M., Kato, et al., *Bull. Chem. Soc. Japan* 42, 3205–3208 (1967). To a cooled solution (0°C.) of 2 mmol $POCl_3$ in 3–4 ml $(CH_3O)_3PO$ the nucleoside (1 mmol) was added stepwise with stirring, the reaction temperature being held constant between 0° and 5° C. The progress of the reactions was monitored by means of HPLC using a Mono Q HR 5/5 anion exchange column (Pharmacia, Uppsala, Sweden). Typically 5 μl of the reaction mixture was neutralized with aqueous sodium hydroxide (final pH 7), and injected on the column. Elution was performed as follows: washing with water, elution with 0.1M $NH_4HCO_3$ which elutes the nucleoside-5'-monophosphate, followed by a linear gradient of 0.1–0.6M $NH_4HCO_3$, which elutes some higher phosphorylated products. The reaction was mostly completed within 45 to 75 minutes as judged by this method, and the reaction product was hydrolyzed and neutralized with 2 volumes of aqueous sodium hydroxide to a final pH of 7. Purification was as described above for the analysis of the reaction mixture. By this method, 10–20 mg of nucleoside-5'-monophosphate could be purified. Larger amounts were purified on a Sepharose Q fast flow column using the same elution conditions.

C. Synthesis of 1,2-dipalmitoyl-sn-glycero-3-phosphoromorpholidate

Dipalmitoylphosphatidic acid (950 mg, 1.47 mmol) was prepared from its disodium salt, essentially as described in Example 1, Part B. Free phosphatidic acid was dissolved in 30 ml chloroform, and the obtained solution was transferred to a two-neck round bottom flask, which contained 30 ml tertbutanol, morpholine (0.53 ml, 6 mmol), and distilled water (0.1 ml, 6 mmol). This mixture was gently refluxed and a solution of dicyclohexylcarbodiimide (1.20 g, 5.9 mmol) in 30 ml tert-butanol was added stepwise from a dropping funnel within 2 hours. The reaction was monitored by thin layer chromatography using silica 60A F254 TLC plates and chloroform/methanol/ammonium hydroxide/water (80:20:1:1 v/v) as eluent (Rf=0.53). The solvent was evaporated under vacuum and the residue was added to 50 ml water. This aqueous suspension was extracted five-times with 75-ml portions of chloroform. The chloroform layers were collected and evaporated to dryness and then lyophilized from cyclohexane three-times to yield a white foam. This compound was used without further purification in the subsequent synthesis steps.

D. Synthesis of 1-(2'-deoxy-2'-fluoro-β-D-arabinofuranosyl)-5'-monophosphate (FIAU-MP)

FIAU (800 mg, 2.16 mmol) was dissolved in trimethyl phosphate (2 ml) at 45° C. with vigorous stirring. The reaction mixture was cooled to 0° C. under argon and added phosphorus oxychloride (2 ml, 20 mmol) via syringe. The reaction mixture was first stirred at 0° C. for one hour, and then kept at −20° C. for 12 hours. The reaction was monitored by TLC (acetic acid:n-butanol:water, 1:4:1 v/v). FIAU-MP precipitated as a white crystal. The supernatant was discarded and the precipitate was washed with anhydrous ether (5×10 ml). The precipitate was redissolved in water (20 ml) and washed with chloroform (3×20 ml). The aqueous layers were combined and lyophilized to yield crude FIAU-MP (800 mg, 1.83 mmol, 85% yield).

Analysis

The HPLC retention time of FIAU-MP was 15.3 min using a 250×4.6 mm, 5 micron Brownlee silica column eluted with hexane:2-propanol:ammonium hydroxide:water (43:57:3:7, v/v).

The compound had an Rf of 0.32 on silica 60A F254 TLC plate eluted with acetic acid:n-butanol:water (1:4:1, v/v).

$UV_{max}$: 254 nm (hexane:2-propanol:ammonium hydroxide:water, 43:57:3:7, v/v).

E. Coupling of 1,2-dipalmitoyl-sn-glycero-3-phosphoromorpholidate to 1-(2'-deoxy-2'-fluoro-β-D-arabinofuranosyl)-5-iodouracil-5'-monophosphate (FIAU-DP-DPG $2NH_4^+$):

In a 50 ml round bottom flask, anhydrous 1,2-dipalmitoyl-sn-glycero-3-phosphoromorpholidate (400 mg, 0.55 mmol) and FIAU-MP (200 mg, 0.48 mmol) was dissolved in anhydrous pyridine (15 ml). The solution was evaporated to dryness in vacuum 5-times from anhydrous pyridine, and then 7 ml of anhydrous pyridine were added. This solution was stirred at room temperature overnight under argon. The progress of the reaction was monitored by TLC (chloroform:methanol:ammonium hydroxide:water, 70:38:8:2, v/v). The reaction mixture was then evaporated from toluene (4×10 ml). This residue was dissolved in 15 ml of chloroform:methanol:water (2:3:1, v/v), and acidified to pH 3 with 0.1N hydrochloric acid. Two layers formed, and the aqueous layer was washed with chloroform (2×10 ml). The combined organic layers were evaporated to dryness, and the residue was dissolved in chloroform:methanol:water (2:3:1, v/v) and applied to a DEAE Sephadex (acetate form) column (2.8×30 cm). [DEAE-Sephadex acetate form was washed with 50% aqueous methanol and then methanol prior to packing in chloroform:methanol:water (2:3:1).] The column was eluted with 250 ml of chloroform:methanol:water (2:3:1, v/v) and then with a linear gradient (1 liter in each reservoir) of 0–0.02M ammonium acetate made up in the same solvent. Fractions containing the product as judged by TLC were pooled and concentrated to 60 ml. This mixture was extracted with chloroform (5×50 ml), and the organic layer was evaporated to yield FIAU-DP-DPG as the diammonium salt.

Analysis

The HPLC retention time of FIAU-DP-DPG diammonium salt was 12.65 min. using a 250×4.6 mm, 5 micron Brownlee silica column eluted with hexane:2-propanol:ammonium hydroxide: water (43:57:3:7, v/v) as the developing system. The compound had an Rf of 0.23 on silica 60A F254 TLC plate eluted with chloroform:methanol:ammonium hydroxide:water (70:28:8:2, v/v).

P: 6.3%, $UV_{max}$: 275 nm, E=5.9×103 (10% methanol in chloroform).

EXAMPLE 2a: dideoxycytidine diphosphate dilauroylglycerol, ddC-DP-DLG; EXAMPLE 2b: dideoxycytidine diphosphate dimyristoylglycerol, ddC-DP-DMG; EXAMPLE 2c: dideoxycytidine diphosphate dipalmitoylglycerol, ddC-DP-DPG; EXAMPLE 2d: dideoxycytidine diphosphate distearoylglycerol, ddC-DP-DSG;

EXAMPLE 2e: 1-(2'-deoxy-2'-fluoro-1-β-arabinosyl)-5-iodocytosine diphosphate dilauroylglycerol, FIAC-DP-DLG; EXAMPLE 2f: 1-(2'-deoxy-2'-fluoro-1-β-arabinosyl)-5-iodocytosine diphosphate dimyristoylglycerol, FIAC-DP-DMG; EXAMPLE 2g: 1-(2'-deoxy-2'-fluoro-1-β-arabinosyl)-5-iodocytosine diphosphate dipalmitoylglycerol, FIAC-DP-DLG; EXAMPLE 2h: 1-(2'-deoxy-2'-fluoro-1-β-arabinosyl)-5-iodocytosine diphosphate distearoylglycerol, FIAC-DP-DSG;

EXAMPLE 2i: 1-(2'-deoxy-2'-fluoro-1-β-arabinosyl)-5-iodouracil diphosphate dilauroylglycerol, FIAU-DP-DLG; EXAMPLE 2j: 1-(2'-deoxy-2'-fluoro-1-β-arabinosyl)-5-iodouracil diphosphate dimyristoylglycerol, FIAU-DP-DMG; and EXAMPLE 2l: 1-(2'-deoxy-2'-fluoro-1-β-arabinosyl)-5-iodouracil diphosphate distearoylglycerol, FIAU-DP-DLG are prepared according to the above method except for using an appropriate species of phosphatidic acid in the coupling step. All the compounds of Examples 2a through 2 1 are worked up and purified in the manner described.

EXAMPLE 3

In vitro Efficacy of Antiviral Liponucleotides in HEP G2.2.15 Cells

A. Assay Protocol

A human hepatoblastoma cell line transfected with a plasmid carrying HBV DNA, HEPG2.2.15, carrying 4 copies of the HBV genome as chromosomally integrated sequences and chronically producing HBV (Acs et al., Proc. Natl. Acad. Sci. USA 84:8581 (1987) was incubated with varying concentrations of test compounds as indicated in Tables 1 and 2 below for 10 days at 37° C. Samples of culture medium were periodically collected and stored for later extracellular HBV DNA analysis. On the 10th day, test cells were lysed for analysis of intracellular HBV genomic forms. HBV DNA was analyzed in a quantitative manner for (i) overall levels of both intracellular and extracellular DNA); and (ii) the relative rate of HBV replication (intracellular DNA only).

(1) Cell culture and treatment: HEPG2.2.15 cells were seeded in 6-well culture plates and grown to confluence over a 10 day period in medium with 5% FBS. Test compounds, comprising antiviral nucleotides and corresponding antiviral liponucleotides were added daily for a continuous 10 day period in medium with 1% dialyzed FBS. (This reduced serum level does not affect HBV replication in confluent cultures of 2.2.15 cells and helps to eliminate uncontrolled variations of endogenous low molecular weight compounds, such as nucleosides, present in FBS). Culture medium, changed daily during the treatment period, was collected and stored for analysis of extracellular (virion) HBV DNA from days 0, 3, 6, and 10 of the treatment period. The culture medium was changed daily during the treatment period to (1) prevent the buildup of potentially toxic metabolites derived from the test compounds; and (2) provide an analysis of HBV virion production during discrete 24-hour intervals which enables a quantitative comparison of any effect on virion production. Compounds were tested in duplicate cultures at 3 concentrations, covering a 100-fold range. Treated cells were lysed following the 10th day of treatment for the analysis of intracellular HBV genomic forms. Untreated cells were maintained as negative controls.

(2) HBV DNA analysis: The analysis of HBV DNA is performed using blot hybridization techniques (Southern and slot blot) and ($^{32}$P)-labelled HBV specific probes. HBV DNA levels were measured by comparison to known amounts of HBV DNA standards applied to every nitrocellulose filter (gel or slot blot). An AMBIS Beta Scanner, which measures the radioactive decay of the hybridized probe directly from the nitrocellulose membranes, was used for the quantitative analysis. Standard curves, generated by multiple analyses, were used to correlate CPM measurements with relative levels of target HBV DNA.

The levels of HBV DNA in each of three classes of intracellular viral genomic forms was individually quantitated; integrated HBV DNA (Integ), episomal monomeric genomes (Mono), and HBV DNA replication intermediates (RI). The levels of the episomal monomeric HBV genes and RI were used as an indicator of the relative level of HBV replication. Inhibition of HBV DNA replication is indicated by the loss of RI without changes in the level of integrated DNA. The levels of HBV virion DNA released into the medium were analyzed by a slot blot hybridization procedure. HBV DNA levels were then compared to levels at day 0 to determine the efficacy of drug treatment.

Both intracellular and extracellular HBV DNA were analyzed in order to (i) allow for verification of compound efficacy, and (ii) provide possible data on the target site in the HBV replication pathway for the compound from examination for the pattern of viral replicative forms.

(3) Controls and interpretation: A steady state level of HBV DNA was maintained in the untreated cells over the challenge period. The daily variation of extracellular HBV DNA production was less than 3-fold, although the levels between different plates was found to vary more. These are the normal variations in HBV virion production usually observed for these cells. Due to the inherent variation of HBV DNA, both intracellular and extracellular depressions of HBV DNA of less than 10-fold for extracellular HBV DNA and 5-fold for intracellular DNA are not considered to be conclusive. Integrated HBV DNA was used to normalize the relative amounts of DNA in each lane because the levels of this class of HBV DNA were expected to remain constant on a per cell basis, and were thus used as a verifying parameter to insure that equal amounts of cellular DNA were compared between separate samples. For reference, the manner in which the hybridization analyses were performed for these experiments results in an equivalence of approximately 1.0 pg/ml of extracellular HBV DNA to 3–5 genomic copies per cell and 1.0 pg/ml of extracellular HBV DNA to $3\times10^5$ viral particles/ml. Typical values for extracellular HBV DNA in untreated cells generally range from 50 to 150 pg/ml; intracellular HBV DNA replication intermediates in untreated cells generally range from 50 to 10 pg/μg cell DNA (average approximately 760 pg/μg).

B: Evaluation of Lipid Derivatives of FMAU, FIAU, and FIAC in 2.2.15 Cell Cultures Cells carrying HBV DNA and chronically producing HBV DNA, as described above, were treated with test compounds as indicated in Table 1 and HBV DNA determined in accordance with the protocol.

TABLE 1

Effect of Test Compounds on HBV Production in HEP G2.2.15 Cell Cultures.

| | TREATMENT | Intracellular HBV DNA† (PG/UG Cell DNA) | | | HBV DNA In Culture Medium (pg/ml) | | | |
|---|---|---|---|---|---|---|---|---|
| | | INTEG. | MONO | RI | DAY 0 | DAY 3 | DAY 6 | DAY 9 |
| 40A | UNTREATED CELLS | 0.8 | 2.5 | 96 | 47 | 110 | 67 | 51 |
| 40B | | 0.8 | 2.1 | 110 | 26 | 70 | 71 | 97 |
| 40C | ARA-A 50 uM | 1.4 | 0.1 | 0.1 | 82 | 1 | 0 | 0 |
| 40D | | 0.9 | 0.3 | 0.2 | 140 | 11 | 0 | 0 |
| 40E | FMAU 50 uM | 1.0 | 1.1 | 1 | 72 | 22 | 0 | 0 |

TABLE 1-continued

Effect of Test Compounds on HBV Production in HEP G2.2.15 Cell Cultures.

| TREATMENT | | Intracellular HBV DNA† (PG/UG Cell DNA) | | | HBV DNA In Culture Medium (pg/ml) | | | |
|---|---|---|---|---|---|---|---|---|
| | | INTEG. | MONO | RI | DAY 0 | DAY 3 | DAY 6 | DAY 9 |
| 40F | | 1.1 | 1.1 | 1 | 79 | 36 | 1 | 0 |
| 40G | FIAU 50 uM | 1.2 | 0.6 | 0.3 | 120 | 59 | 0.3 | 0 |
| 40H | | 1.4 | 0.3 | 1 | 56 | 26 | 0 | 0 |
| 40I | DMP-FIAU 100 uM | 1.2 | 1.1 | 1 | 52 | 10 | 3 | 0 |
| 40J | | 1.3 | 0.5 | 3 | 64 | 3 | 0.2 | 0 |
| 40K | DPP-FIAU 100 uM | 0.7 | 1.0 | 9 | 80 | 110 | 33 | 5 |
| 40L | | 0.6 | 1.6 | 8 | 72 | 25 | 111 | 4 |
| 40M | FIAU-DP-DPG 100 uM | 0.9 | 2.5 | 21 | 56 | 81 | 22 | 8 |
| 40N | | 1.2 | 1.4 | 19 | 89 | 100 | 16 | 10 |
| 40O | FIAC 50 uM | 1.0 | 1.0 | 4 | 82 | 37 | 4 | 0.4 |
| 40P | | 1.2 | 1.3 | 2 | 76 | 41 | 2 | 0 |
| 40Q | DMP-FIAC 100 uM | 0.9 | 2.9 | 100 | 43 | 59 | 77 | 97 |
| 40R | | 1.2 | 2.1 | 93 | 110 | 66 | 53 | 59 |
| 40S | DPP-FIAC 100 uM | 1.3 | 1.5 | 3 | 89 | 44 | 9 | 1 |
| 40T | | 0.9 | 2.8 | 7 | 87 | 35 | 3 | 0.1 |
| 40U | FIAC-DP-DPG 100 uM | 0.7 | 1.5 | 10 | 68 | 71 | 5 | 1 |
| 40V | | 1.0 | 2.1 | 12 | 72 | 29 | 7 | 3 |
| 40W | DOPC CONTROL 100 Um | 0.8 | 2.1 | 95 | 42 | 25 | 36 | 44 |
| 40X | | 1.2 | 2.3 | 80 | 53 | 47 | 60 | 92 | ara-A: adenosine-9-β-D-arabinofuranoside
FMAU: , 1-(2'-deoxy-2'-fluoro-1-β-D-arabinofuranosyl)-5-methyluracil
FIAU: 1-(2'-deoxy-2'-fluoro-1-β-D-arabinofuranosyl)-5-iodouracil
FIAC: 1-(2'-deoxy-2'-fluoro-1-β-arabinosyl)-5-iodocytosine
MP: monophosphate
DP: diphosphate
DMP-FIAU: dimyristoylphosphatidyl-FIAU
DPP-FIAU: dipalmitoyl phosphatidyl-FIAU
FIAU-DP-DPG: FIAU diphosphate dipalmitoyl glycerol
DMP-FIAC: dimyristoylphosphatidyl-FIAC
DPP-FIAC: dipalmitoylphosphatidyl-FIAC
FIAC-DP-DPG: FIAC diphosphate dipalmitoylglycerol
DOPC: Control: dioleoylphosphatidylcholine liposomes without added drug.
†Analysis of intracellular HBV DNA was 24 hours following the 10th day of treatment.

Summary of Table 1 Results (a) Positive treatment controls, ara-A(adenosine-9-β-D-arabinofuranoside), FIAU, FIAC, and FMAU, all produced significant depression of HBV DNA replication. Levels of HBV DNA in the culture medium were reduced by day 3, and were very low or undetectable by days 6 and 9.

(b) All of the lipid prodrugs of FIAC and FIAU exhibited antiviral activity in the assay. DMP-FIAU (40I, 40J) was the most active lipid compound, reducing viral DNA in the medium to an undetectable level at day 9. DPP-FIAC (40S, 40T), DPP-FIAU (40K, 40L), FIAC-DP-DPG (40U, 40V), and FIAU-DP-DPG (40M, 40N) also exhibited substantial degrees of activity, while DMP-FIAC (40S, 40R) was less active.

(c) Treatment with dioleylphosphatidylcholine (DOPC) lipid control alone showed no significant effects on HBV DNA replication (40W, 40X).

C: Evaluation of Lipid Derivatives of ddC in 2.2.15 Cell Cultures

Cells carrying HBV DNA and chronically producing HBV DNA, as described above, were treated with test compounds as indicated in Table 2 and HBV DNA determined in accordance with the protocol.

TABLE 2

Effect of Test Compounds on HBV Replication in HEP G2.2.15 Cell Cultures.

| | TREATMENT | Intracellular HBV DNA† (PG/UG Cell DNA) | | | HBV DNA in Culture Medium (pg/ml) | | | |
|---|---|---|---|---|---|---|---|---|
| | | INTEG. | MONO | RI | DAY 0 | DAY 3 | DAY 6 | DAY 9 |
| 45A | Untreated Cells | 1.4 | 2.2 | 77 | 130 | 68 | 74 | 110 |
| 45B | | 1.1 | 2.4 | 52 | 83 | 85 | 54 | 71 |
| 45C | 2'3'ddC 100 uM | 1.2 | 0.5 | 0.1 | 140 | 54 | 11 | 0 |
| 45D | | 1.4 | 0.3 | 0.1 | 130 | 56 | 5 | 0 |
| 45E | 2'3'ddC 30 uM | 1.2 | 0.4 | 0.1 | 79 | 21 | 5 | 0 |
| 45F | | 1.0 | 0.7 | 0.1 | 51 | 36 | 4 | 0 |
| 45G | 2'3'ddC 10 uM | 1.0 | 1.3 | 1 | 110 | 52 | 21 | 1 |
| 45H | | 1.3 | 1.1 | 1 | 51 | 88 | 17 | 1 |
| 45I | DOPC control only | 1.0 | 2.2 | 64 | 86 | 51 | 59 | 78 |
| 45J | | 1.3 | 2.0 | 79 | 52 | 52 | 85 | 66 |

TABLE 2-continued

Effect of Test Compounds on HBV Replication in HEP G2.2.15 Cell Cultures.

| | TREATMENT | Intracellular HBV DNA† (PG/UG Cell DNA) | | | HBV DNA in Culture Medium (pg/ml) | | | |
|---|---|---|---|---|---|---|---|---|
| | | INTEG. | MONO | RI | DAY 0 | DAY 3 | DAY 6 | DAY 9 |
| 45K | DOP 2'3'ddC 100 uM | 1.0 | 0.4 | 0.3 | 75 | 24 | 0 | 0 |
| 45L | | 1.2 | 0.6 | 0.1 | 89 | 15 | 0 | 0 |
| 45M | DOP 2'3'ddC 30 uM | 0.9 | 0.4 | 1 | 90 | 46 | 13 | 0 |
| 45N | | 1.2 | 0.9 | 0.3 | 58 | 5S | 17 | 0 |
| 45O | DOP 2'3'ddC 10 uM | 1.0 | 1.6 | 51 | 77 | 60 | 48 | 26 |
| 45P | | 1.2 | 2.0 | 39 | 84 | 120 | 74 | 24 |

†Analysis or intracellular HBV DNA was 24 hours following the 10th day or treatment. Data indicates an undetectable level of HBV DNA when sensitivity cutoff was 0.1 pg/ml.
ddC: dideoxycytidine
DOPC: dioleoylphosphatidylcholine (a lipid control without drug)
DOP-2', 3'ddC: dioleoylphosphatidyl-ddC Summary of Table 2 Results The positive treatment control, 2',3' ddC(2',3'-dideoxycytosine) produced a significant depression of HBV DNA replication. The test compound dioleoylphosphatidyl-ddC (DOP-ddC) is a potent inhibitor of HBV DNA replication. Extracellular HBV DNA was undetectable by day 9 (>1000-fold depression versus the day 0 values) and approximately a 100-fold depression of intracellular HBV DNA replication intermediates was observed after 9 days of treatment at the highest concentrations used.

EXAMPLE 4

Pharmacokinetics of Phosphatidyl-[$^3$H]ddC in Mice

Dioleoylphosphatidyl-ddC was synthesized by coupling [$^3$H]ddC (5 Mc$_i$/mol) to dioleoylphosphatidic acid as described in Example 1.

Unilamellar lipid vesicles were prepared using dioleoylphosphatidylcholine/cholesterol/phosphatidyl-[$^3$H]ddC in a molar ratio of 67/30/3 by the method of Mayer, L. D., Hope, M. J., and Cullis, P. R. (18), using a 200 nanometer NUCLEOPORE™ filter. Smaller vesicles may be prepared by the same method using a 100 nanometer NUCLEOPORE™ filter, or by microfluidization as described by Mayhew, E., et al. (16).

Figure 1:
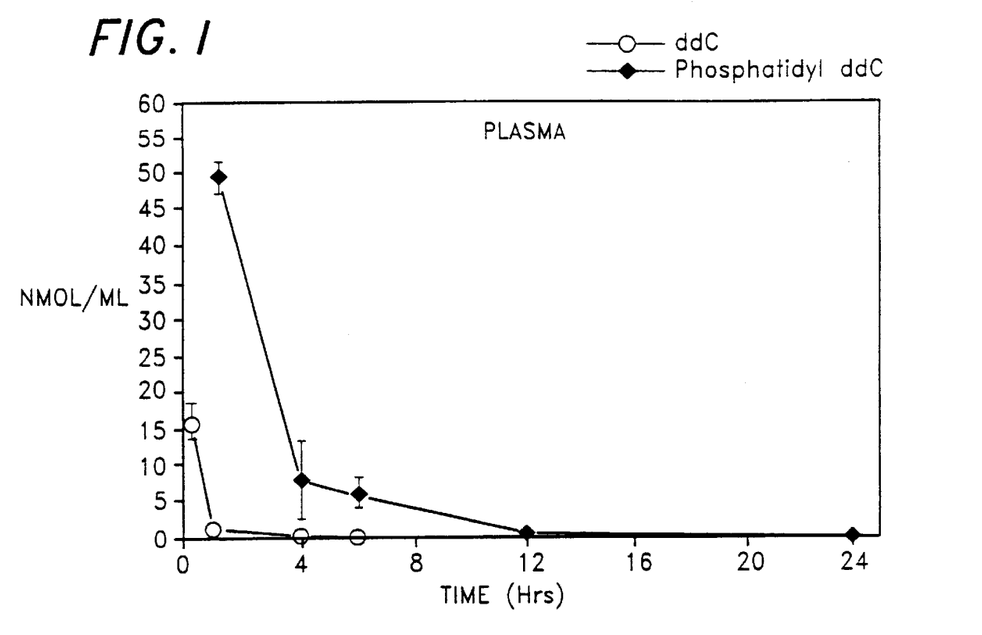
FIG. 1 is a graph showing the comparative levels of ddC in plasma.
Figure 2:
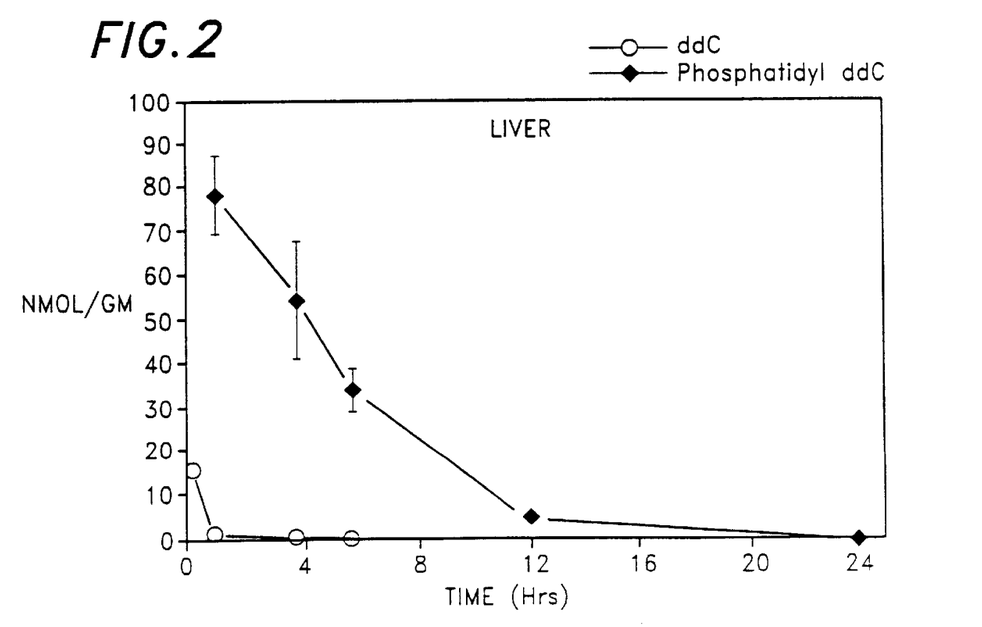
FIG. 2 is a graph showing the comparative levels of ddC in liver.
Figure 3:
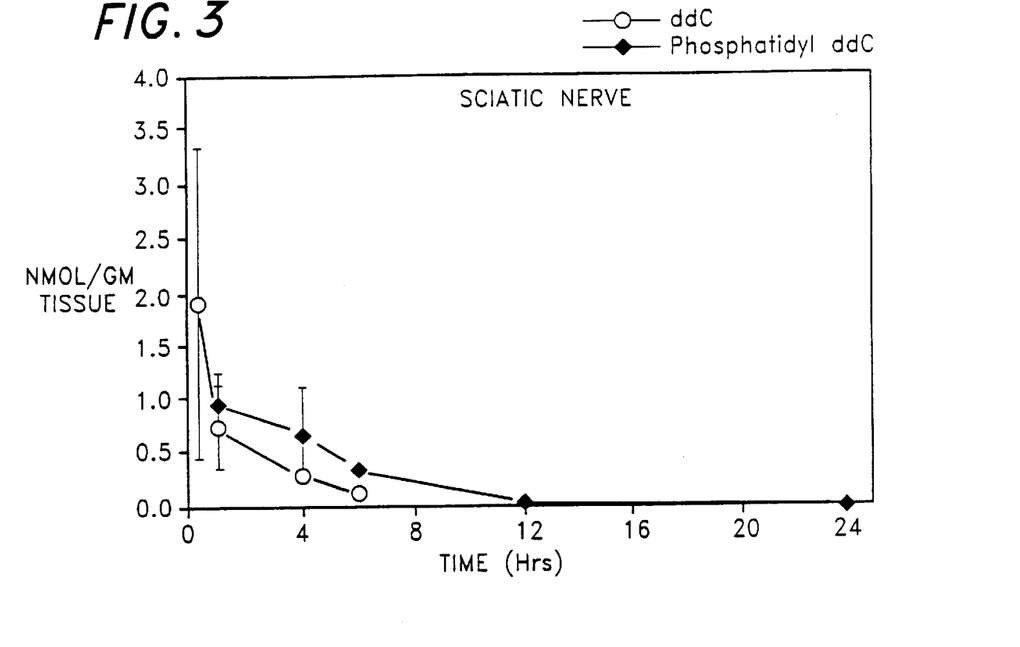
FIG. 3 is a graph showing the comparative levels of ddC in sciatic nerve.

Mice were treated intraperitoneally (i.p.) with 3 mg/kg of [$^3$H]ddC or an equimolar dose of phosphatidyl-[$^3$H]ddC and the animals were sacrificed at various times and blood and tissues were obtained for analysis. The results are shown in FIGS. 2a to 2f as nmol drug/gm of tissue±std. dev. (n=3).

DdC was cleared rapidly from plasma in the first hour while phosphatidyl-ddC reached much higher levels (50 versus 16 nmol/ml) and persisted much longer in the circulation (FIG. 2a). The area under the curve (AUC) for phosphatidyl-ddC was substantially larger than that of ddC. The peak liver level for ddC was 18 nmol/gm at 15 min., while phosphatidyl-ddC reached a peak level at 1 hr of about 80 nmol/gm. The AUC in liver for phosphatidyl-ddC was 42 times greater than that of ddC (FIG. 2b). Spleen levels were also much higher with phosphatidyl-ddC (AUC 85 times greater than ddC, FIG. 2f).

In sciatic nerve and brain, toxicity targets of ddC in man, the levels were not greatly increased with phosphatidyl-ddC as compared to ddC; AUC values in sciatic nerve were 1.7 times greater than with ddC (FIG. 2c), and the differences were not significant at most time points. Brain levels of phosphatidyl-ddC were increased slightly (2.7x; FIG. 2d); however, it should be noted that the brain was not perfused to remove blood, which may be responsible for the apparent increase.

Similar results, comprising a targeting of antiviral agent to the cells of the liver as determined by increased liver uptake and retention of AZT, were observed when liposomal phosphatidyl AZT (p-AZT) was administered intraperitoneally to mice.

EXAMPLE 5

Treatment of Hepatitis B Infection in a Human Patient

A patient suffering from active hepatitis B infection is treated by parenteral administration of liposomally incorporated DMP-FIAU at a dose of 1 mg/kilo/day of the active FIAU moiety until a clinical response indicating the inhibition of production of hepatitis B virus is observed. Liposomes incorporating DMP-FIAU are prepared using a microemulsification apparatus (MICROFLUIDIZER®microemulsifier, Newton, Mass.), as indicated in Example 6. The dose of FIAU can be adjusted from 1/100th of the indicated dose to 10 times the indicated dose, as determined by clinical judgment. An effective response to hepatitis therapy with DMP-FIAU lipid prodrug is measured by absence of detectable virus particles in the serum of the patient and clinical improvement in the patient.

EXAMPLE 6

Preparation and sizing of Liposomes containing Antiviral Liponucleotides

A quantity of 6.42 micromoles of dioleoylphosphatidylcholine, 3.85 micromoles of cholesterol, and 1.28 micromoles of dioleoylphosphatidyl-dideoxycytidine (DOP-ddC) were mixed in a sterile 2.0 ml glass vial and the solvent was removed in vacuo in a rotary evaporator. In some experiments, dioleoylphosphatidyl-dideoxycytidine was replaced by DMP-FIAU or FIAC-DP-DPG; control liposomes were prepared by omitting the antiviral liponucleotide. The dried film was put under high vacuum overnight at room temperature to remove traces of solvent. The lipid film was hydrated at 30° C. with 0.3 ml of sterile 10 Mm sodium acetate buffer (pH 5.0) containing isotonic dextrose and the ampule was sealed. The mixture was vortexed intermittently for 10 minutes followed by sonication using a Heat Systems Ultrasonics sonicator with a cup horn generator (431B) at output control setting #9 for 90 to 120 minutes at which time the sample is clarified, and diluted with buffer for use.

Alternatively, the lipid film was hydrated by the addition of 1.0 ml of sterile phosphate buffered saline, and the mixture was shaken gently at 20° C. for 20 minutes, followed by ten 30-second cycles of vortexing to form multilamellar liposomes. The suspension of liposomes was subjected to 5 cycles of extrusion through two stacked Nuclepore® polycarbonate filters having pore diameters of 200 nm, to form a homogenously sized liposomal population. A liposomal population having an approximate mean diameter of 0.2 µm to 0.1 µm or less is prepared by processing the hydrated lipid suspension in a MICROFLUIDIZER® microemulsifier apparatus. The size distribution of the particles can be regulated by varying the time of microemulsification from about 2 up to about 10 minutes as described by Mayhew, E. et al. (16).

It should be apparent from the foregoing that other nucleoside analogues and lipid derivatives thereof can be substituted in the Examples to obtain similar results. It should be further emphasized that the present syntheses are broadly applicable to formation of compounds from essentially all antihepatitis B nucleosides for use in the invention.

Accordingly, the invention may be embodied in other specific forms without departing from it in spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within their scope.

REFERENCES

1. Lee, B. et al., *Antimicrobial Agents and Chemotherapy* 33:336–339(1989).
2. Kassanides, C. et al., *Gastroenterology* 97:1275–80 (1989).
3. Hantz, O. et al., *Antiviral Research* 4:187–199(1984).
4. Hess, G. et al., *Antimicrobial Agents and Chemotherapy* 19(1)44–50(1981).
5. Matthes, E. et al. *Antimicrobial Agents and Chemotherapy* 34:1986–1990 (1990)
6. Rosenthal, A. and Geyer, R., *Journal of Biol. Chem.* 235(8)2202–2206(1960).
7. Yoshikawa, et al., *Tetrahedron Lett.* 50, 5065–5068 (1967).
8. Yoshikawa, M., Kato, et al., *Bull. Chem. Soc. Japan* 42, 3205–3208 (1967).
9. Toorchen, D. and Topal, M. D. (1983) *Carcinogenesis,* 4: 1591–1597.
10. Brown, D. A., Malkin T. and Maliphant, G. K. (1955) *J. Chem. Soc.* (London) pp.1584–1588.
11. Agranoff, B. W. and Suomi, W. D. (1963) *Biochem. Prep.,*10:46–51.
12. Spanjer, H. et al., *Biochim. Biophys. Acta* 863:24–230 (1986).
13. Bangham, A. D., Standish, M. M. and Watkins, J. C. (1965) *J. Mol. Biol.,* 23:238–252.
14. Olson, F., Hunt, C. A. Szoka, F. C., Vail, W. J. and Papahadjopoulos, D. (1979) *Biochim. Biophys. Acta,* 557:9–23.
15. Szoka, F., and Papahadjopoulos, D. (1978) *Proc. Nat. Acad. Sci.* 75:4194–4198.
16. Mayhew, E., Lazo, R., Vail, W. J., King, J., Green, A. M. *Biochim. Biophys. Acta,* (1984) 775:169–175.
17. Kim, S., Turker, M., Chi, E., et al., *Biochim. Biophys. Acta,* 728:339:348.
18. Mayer, L. D., Hope, M. J. and Cullis, P. R. (1986) *Biochim. Biophys. Acta,* 858:161–168.
19. Fukanaga, M., Miller, M. M., Hostetler, K. Y. and Deftos, L. J. (1984) *Endocrinol.*16:757–761.
20. Sherphof, G. L. et al., *NATO ASI Series, Ser. A: Targeting Drugs: Anatomical and Physiological Considerations* 155:109–120 (1988)
21. Sherphof, G. L. et al., *Lipids* 22(11)891–896 (1987)

What is claimed is:

1. A method of treating hepatitis B infection in a mammal, comprising administering to said mammal an effective dose of a hepatitis B virus reverse transcriptase-inhibiting compound comprising:

a nucleoside analogue having the ability to inhibit the replication of hepatitis B virus, selected from the group consisting of dideoxynucleosides, didehydronucleosides, acyclic nucleosides, nucleosides wherein a carbon atom of the purine or pyrimidine base or the pentose group of the nucleotide analogue has been halogenated, methylated or aminated, and nucleoside analogues wherein the pentose group is a furanose wherein at least one carbon atom of said furanose has been halogenated; and at least one lipid moiety, selected from the group consisting of mono- or diacylglycerols, mono- or dialkylglycerols, 1-acyl,2-alkylglycerols, 1-alkyl,2-acylglycerols, sphingolipids, fatty acids and alcohols, ceramides, or 1,2-acyl, 1,2-alkyl or acyl/alkyl-substituted oxypropyl(dimethyl)-β-hydroxyethyl ammonium, covalently linked through a phosphate group to an available functional group at the 5'-carbon or the 3'-carbon of said pentose group.

2. A method of inhibiting the replication of hepatitis B virus in a cell, said virus having established an infection in said cell, comprising contacting said cell with an effective dose of a hepatitis B virus reverse transcriptase-inhibiting compound comprising:

a nucleoside analogue having the ability to inhibit the replication of hepatitis B virus, selected from the group consisting of dideoxynucleosides, didehydronucleosides, acyclic nucleosides, nucleosides wherein a carbon atom of the purine or pyrimidine base or the pentose group of the nucleotide analogue has been halogenated, methylated or aminated, and nucleoside analogues wherein the pentose group is a furanose wherein at least one carbon atom of said furanose has been halogenated; and at least one lipid moiety, selected from the group consisting of mono- or diacylglycerols, mono- or dialkylglycerols, 1-acyl,2-alkylglycerols, 1-alkyl,2-acylglycerols, sphingolipids, fatty acids and alcohols, ceramides or 1,2-acyl, 1,2-alkyl or acyl/alkyl-substituted oxypropyl(dimethyl)-β-hydroxyethyl ammonium, covalently linked through a phosphate group to an available functional group at the 5'-carbon or the 3'-carbon of said pentose group.

3. The method of claim 1, wherein said lipid moiety is a glycerolipid comprising one or two aliphatic groups, each aliphatic group having from two to twenty-four carbon atoms and said aliphatic groups are independently attached to the glycerol structure of said glycerolipid by ester, thioester, ether, thioether or vinyl ether bonds.

4. The method of claim 2 or 3, wherein said hepatitis B virus infection is in a human cell, and said compound is phosphatidyl-dideoxycytidine (p-ddC).

5. A method of delivering an active mono-, di- or triphosphate of a hepatitis B virus-inhibiting nucleotide analogue to a cell to inhibit hepatitis B virus replication, said analogue selected from the group consisting of dideoxycytidine (ddC), 1-(2'-deoxy-2'-fluoro-1-β-D-arabinofuranosyl)-5-iodocytosine (FIAU), 1-(2'-deoxy-2'-fluoro-1-β-D-arabinofuranosyl)-5-iodocytosine (FIAC), or 1-(2'-deoxy-2'-fluoro-1-β-D-arabinofuranosyl)-5-methyluracil (FMAU) to a cell, comprising delivering to said cell the lipid prodrug of said nucleoside phosphate analogue, and permitting the enzymatic cleavage of said prodrug to deliver said active phosphate to said cell.

6. The method of claim 2 or 3, wherein said infection is in a human cell and said compound comprises 1-O-stearoyl-rac-3-glycerol attached to an antihepatitis B nucleoside analogue through a phosphate group.

7. The method of claim 2 or 3, wherein said lipid derivatives of nucleoside analogues are incorporated into liposomes.

8. The method of claim 7 wherein substantially all of said liposomes have a diameter less than about 100 nanometers, with a mean diameter of from about 30 to 80 nanometers.

9. The method of claim 2 or 3, wherein said lipid derivatives are in the form of dispersed phase droplets in a microemulsion.

10. The method of claim 1 or 3, wherein said compound is administered parenterally to a mammal.

11. The method of claim 10 wherein said compound is administered intravenously, subcutaneously, intramuscularly, or intraperitoneally.

12. The method of claim 1 or 3, wherein said compound is administered orally to a mammal.

13. The method of claim 1 or 3, wherein said liposomes are sized appropriately to pass through the hepatic sinusoids and to be selectively taken up by hepatocytes and targeted to the reservoir of infection.

* * * * *